United States Patent
Negishi

(10) Patent No.: US 7,807,277 B2
(45) Date of Patent: Oct. 5, 2010

(54) AMINE COMPOUND AND ORGANIC LIGHT-EMITTING DEVICE

(75) Inventor: Chika Negishi, Yokosuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 411 days.

(21) Appl. No.: 11/941,585

(22) Filed: Nov. 16, 2007

(65) Prior Publication Data
US 2008/0124573 A1   May 29, 2008

(30) Foreign Application Priority Data
Nov. 28, 2006   (JP) .............................. 2006-320084

(51) Int. Cl.
*H01L 51/54* (2006.01)
*H01J 1/62* (2006.01)
*C07C 211/44* (2006.01)

(52) U.S. Cl. .................. 428/690; 428/917; 313/504; 313/506; 564/427

(58) Field of Classification Search .................. None
See application file for complete search history.

(56) References Cited

U.S. PATENT DOCUMENTS

| | | | |
|---|---|---|---|
| 5,061,569 A | 10/1991 | VanSlyke et al. | 428/457 |
| 6,280,859 B1 | 8/2001 | Onikubo et al. | 428/690 |
| 6,517,957 B1 | 2/2003 | Senoo et al. | 428/690 |
| 6,833,200 B2 | 12/2004 | Senoo et al. | 428/690 |
| 6,858,325 B2 | 2/2005 | Senoo et al. | 428/690 |
| 7,589,218 B2 * | 9/2009 | Zhang | 549/344 |
| 2001/0033944 A1 | 10/2001 | Onikubo et al. | 428/690 |
| 2005/0025997 A1 | 2/2005 | Senoo et al. | 428/690 |
| 2006/0286408 A1 | 12/2006 | Suzuki et al. | 428/690 |
| 2008/0145699 A1 * | 6/2008 | Yabe et al. | 428/690 |
| 2009/0236973 A1 * | 9/2009 | Yabe et al. | 313/504 |

FOREIGN PATENT DOCUMENTS

| | | |
|---|---|---|
| JP | 10-251633 | 9/1998 |
| JP | 2851185 | 11/1998 |
| JP | 2000-016973 | 1/2000 |
| JP | 2001-039933 | 2/2001 |
| JP | 2002-265938 | * 9/2002 |
| JP | 3508984 | 1/2004 |

(Continued)

OTHER PUBLICATIONS

JPO machine translation for JP 2004-171808 published Jun. 2004.*

(Continued)

*Primary Examiner*—Dawn Garrett
(74) *Attorney, Agent, or Firm*—Fitzpatrick, Cella, Harper & Scinto

(57) ABSTRACT

The present invention provides an amine compound useful for an organic light-emitting device capable of realizing extremely high luminous efficiency and having a light output with a long lifetime can be formed. The amine compound is represented by the following general formula (1):

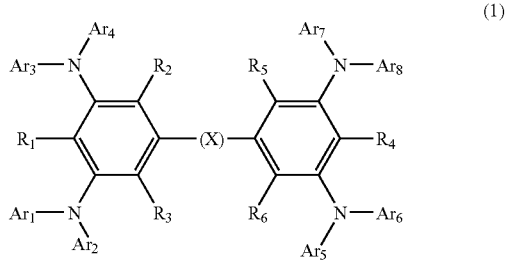

wherein $Ar_1$ to $Ar_8$ each represent an aryl group or a heterocyclic group, $R_1$ to $R_6$ each represent a hydrogen atom, a halogen atom, an alkyl group, or the like, and X represents a biphenylene group, a fluorenylene group, or the like.

3 Claims, 3 Drawing Sheets

FOREIGN PATENT DOCUMENTS

| JP | 2004-171808 | * | 6/2004 |
| WO | WO 2006/062062 | * | 6/2006 |
| WO | WO 2006/067976 | * | 6/2006 |

OTHER PUBLICATIONS

JPO machine translation for JP 2002-265938 published Sep. 2002.*

Miyaura et al., "Palladium-Catalyzed Cross-Coupling Reactions of Organoboron Compounds," *Chemical Reviews*, vol. 95, No. 7, 2457-2483 (1995).

Yamamoto et al., "A Novel Type of Polycondensation Utilizing Transition Metal-Catalyzed C-C Coupling. I. Preparation of Thermostable Polyphenylene Type Polymers," *Chem. Soc. Jpn.*, vol. 51, No. 7, 2091-2097 (1978).

* cited by examiner

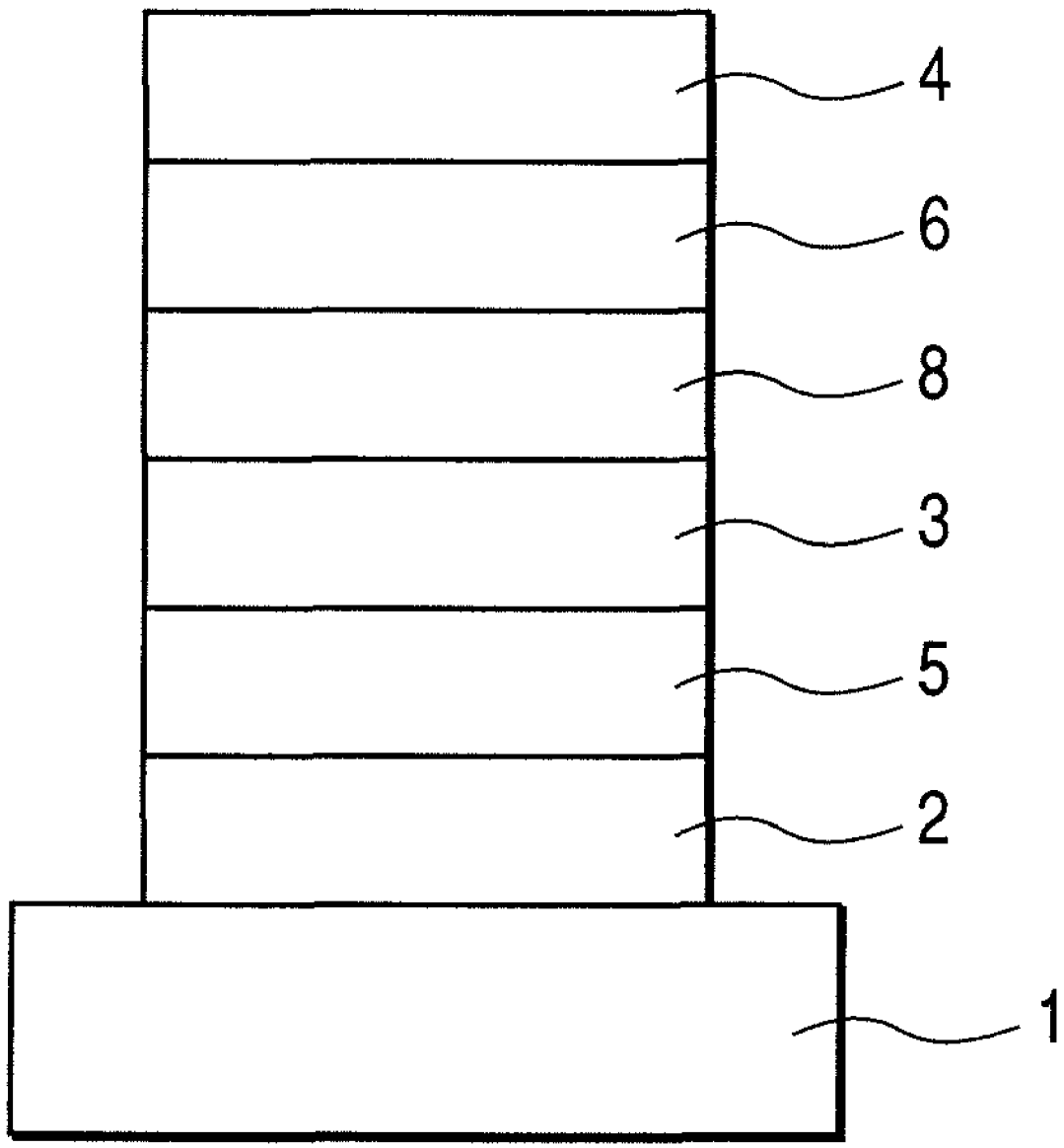

AMINE COMPOUND AND ORGANIC LIGHT-EMITTING DEVICE

BACKGROUND OF THE INVENTION

1. Field of the Invention

The present invention relates to an amine compound and an organic light-emitting device using the same, and more specifically, to a device that radiates light by applying an electric field to a thin film formed of an organic compound.

2. Description of the Related Art

An organic light-emitting device is a device which includes a thin film containing a fluorescent organic compound or a phosphorescent organic compound and interposed between an anode and a cathode. Therefore, a hole and an electron are injected from each of the anode and cathode. Further, an exciton of the fluorescent compound or the phosphorescent compound is generated. The device uses light which is radiated upon return of the exciton to its ground state.

Recent progress of an organic light-emitting device is significant, and it is suggested that the device have potential to find use in a wide variety of applications because of the following reasons. The device has characteristics such as a high luminance at a low applied voltage, a variety of emission wavelengths, and high-speed responsiveness. Furthermore, the device can be a thin, light-weight light-emitting device.

Japanese Patent No. 2851185 discloses, as an example of an organic light-emitting device material of an amine compound and an organic light-emitting device using the material, an organic light-emitting device using a tetraaryldiamine. In addition, Japanese Patent No. 3508984 and Japanese Patent Application Laid-Open No. 2000-016973 disclose, as other examples, organic light-emitting devices each using a diaminofluorene derivative. In addition, Japanese Patent Application Laid-Open No. H10-251633 and Japanese Patent Application Laid-Open No. 2001-039933 disclose, as other examples, organic light-emitting devices each using a diamine compound.

However, at present, an optical output with additionally high luminance, or additionally high conversion efficiency is needed.

SUMMARY OF THE INVENTION

The present invention has been made in view of the above, and an object of the present invention is to provide an amine compound for forming an organic light-emitting device capable of realizing extremely high luminous efficiency and having a light output with a long lifetime, and the organic light-emitting device. Another object of the present invention is to provide an organic light-emitting device that can be easily produced at a relatively low cost.

The inventors of the present invention has made intensive studies in order to attain the above-mentioned objects. As a result, the inventors of the present invention have completed the present invention.

According to the present invention, there is provided an amine compound represented by the following general formula (I):

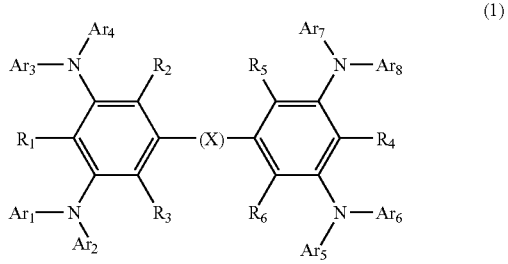

(1)

wherein $Ar_1$ to $Ar_8$ each independently represent a substituted or unsubstituted aryl group, or a substituted or unsubstituted heterocyclic group, and may be the same as or different from one another, and $Ar_1$ and $Ar_2$, $Ar_3$ and $Ar_4$, $Ar_5$ and $Ar_6$, or $Ar_7$ and $Ar_8$ may be bonded to each other to form a ring;

$R_1$ to $R_6$ each represent a hydrogen atom, a halogen atom, an alkyl group, an alkoxy group, an amino group, an aryl group, or a heterocyclic group, and may be the same as or different from one another, and the alkyl group, the alkoxy group, the amino group, the aryl group, and the heterocyclic group which are represented by $R_1$ to $R_6$ may have a substituent; and X represents a substituted or unsubstituted biphenylene or fluorenylene group, or a substituted or unsubstituted divalent heterocyclic group.

An organic light-emitting device using the amine compound of the present invention emits light with high efficiency at a low applied voltage, and provides particularly excellent durability.

Further features of the present invention will become apparent from the following description of exemplary embodiments with reference to the attached drawings.

BRIEF DESCRIPTION OF THE DRAWINGS

FIG. 5 is a sectional view illustrating another example of the organic light-emitting device according to the present invention.

DESCRIPTION OF THE EMBODIMENTS

Figure 1:
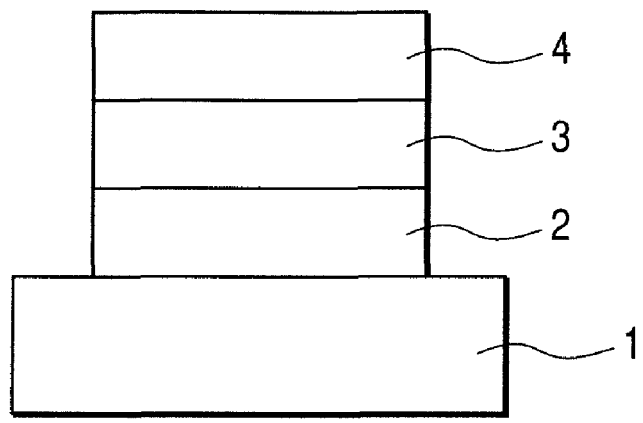
FIG. 1 is a sectional view illustrating an example of an organic light-emitting device according to the present invention.

Hereinafter, the present invention will be described in detail.

An amine compound of the present invention can be used mainly as a material for a hole transport layer or a material for a hole injection layer. When the compound is used for a hole transport layer, the compound can be used to serve as an electron blocking layer, a light-emitting device having high luminous efficiency and a long lifetime can be obtained, and the compound has an effect particularly on a light-emitting device having a long lifetime.

A molecule of the amine compound of the present invention was designed for the purpose of improving the electron blocking property of a hole transport layer. In other words, the molecule was designed while taking account of the fact that the absolute value for the electron affinity of the hole transport layer should be sufficiently small as compared to the absolute value for the electron affinity of a light-emitting layer. Specifically, in order to suppress the extension of the conjugate of the entire skeleton of the molecule, two amino groups on each of both sides of the molecule are subjected to meta coordination on a phenyl group, whereby the band gap of the molecule is enlarged. Further, the molecule is turned into a tetraamine compound, whereby the ionization potential of the molecule is also enlarged, and the absolute value for the electron affinity of the molecule is reduced. In addition, improvement of the property of hole injection from an anode can be expected from the foregoing molecular design because the molecular design is intended for the enlargement of the ionization potential.

Further, the band gap, ionization potential, and electron affinity of the compound can be appropriately adjusted by substituting substituents represented by any one of $Ar_1$ to $Ar_8$ on each amino group. As a result, when a fluorescent material or a phosphorescent material is used in the light-emitting layer, the compound can be converted into a hole transport layer having an ionization potential and an electron affinity which are suitable for each of a blue light-emitting layer, a green light-emitting layer, and a red light-emitting layer.

In addition, when a fluorene derivative group is introduced into at least one of $Ar_1$ to $Ar_8$, the carrier transport property of the compound can be improved, and the Tg of the compound can be increased. Further, the compound to be obtained can be a material having good heat stability, so that an increase in lifetime of a light-emitting device can be expected from the compound.

In addition, the amine compound of the present invention is a tetraamine compound, so that the compound can be easily dissolved in a proper solvent, the solution can be easily formed into a uniform thin film by an application method, and an additional increase in lifetime of the light-emitting device can be expected from the compound.

In addition, the amine compound of the present invention can also be used as a material for a blue light-emitting layer having good chromaticity.

The present invention has been achieved as a result of the molecular design based on the foregoing discussion.

Specific examples of the substituents in the above general formula (1) will be shown below.

Examples of the aryl group represented by $Ar_1$ to $Ar_8$ and $R_1$ to $R_6$ in the general formula (1) include, but of course not limited to, a phenyl group, a naphthyl group, a pentalenyl group, an indenyl group, an azulenyl group, an anthryl group, a pyrenyl group, an indacenyl group, an acenaphthenyl group, a phenanthryl group, a phenalenyl group, a fluoranthenyl group, an acephenanthryl group, an aceanthryl group, a triphenylenyl group, a chrysenyl group, a naphthacenyl group, a perylenyl group, a pentacenyl group, a biphenyl group, a terphenyl group, and a fluorenyl group.

Examples of the heterocyclic group represented by $Ar_1$ to $Ar_8$ and $R_1$ to $R_6$ in the general formula (1) include, but of course not limited to, a thienyl group, a pyrrolyl group, a pyridyl group, an oxazolyl group, an oxadiazolyl group, a thiazolyl group, a thiadiazolyl group, a terthienyl group, a carbazolyl group, an acridinyl group, a phenanthrolyl group, and a dibenzothiophenyl group.

Examples of the halogen atom represented by $R_1$ to $R_6$ in the general formula (1) include fluorine, chlorine, bromine, and iodine.

Examples of the alkyl group represented by $R_1$ to $R_6$ in the general formula (1) include, but of course not limited to, a methyl group, a trifluoromethyl group, an ethyl group, a normal propyl group, an isopropyl group, a normal butyl group, a tertiary butyl group, a secondary butyl group, an octyl group, a 1-adamantyl group, and a 2-adamantyl group.

Examples of the alkoxy group represented by $R_1$ to $R_6$ in the general formula (1) include, but of course not limited to, alkyloxy groups each having the above substituted or unsubstituted alkyl group, and aryloxy groups each having the above substituted or unsubstituted aryl or heterocyclic group such as a methoxy group, an ethoxy group, a propoxy group, a 2-ethyl-octyloxy group, a phenoxy group, a 4-tertiary butylphenoxy group, a benzyloxy group, and a thienyloxy group.

Examples of the amino group (—NR'R") represented by $R_1$ to $R_6$ in the general formula (1) include amino groups having R' and R" which are each represented by a hydrogen atom, or the above substituted or unsubstituted alkyl, aryl, heterocyclic, or aralkyl group.

Specific examples of the amino group include, but of course not limited to, an amino group, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an N,N-diphenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tertiary butylphenyl)amino group, and an N-phenyl-N-(4-trifluoromethylphenyl)amino group.

Examples of substituent that the groups represented by $Ar_1$ to $Ar_8$ and $R_1$ to $R_6$ in the general formula (1) may have include: alkyl groups such as a methyl group, a trifluoromethyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, and a dianisolylamino group; alkoxyl groups such as a methoxyl group, an ethoxyl group, a propoxyl group, and a phenoxyl group; a cyano group; and halogen atoms such as fluorine, chlorine, bromine, and iodine.

Examples of the divalent heterocyclic group represented by X in the general formula (1) include, but of course not limited to, a dibenzofuranylene group, a dibenzothiophenylene group, a furylene group, a pyrrolylene group, a pyridylene group, a terpyridylene group, a thienylene group, a terthienylene group, an oxazolylene group, a thiazolylene group, and a carbazolylene group.

Examples of substituents that X in the general formula (1) may have include: alkyl groups such as a methyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, and a dianisolylamino group; alkoxyl groups such as a methoxyl group, an ethoxyl group, a propoxyl group, and a phenoxyl group; a cyano group; and halogen atoms such as fluorine, chlorine, bromine, and iodine.

It should be noted that a hydrogen atom in any one of the above substituents may be replaced by a deuterium atom.

Next, representative examples of the amine compound of the present invention are shown as exemplified compounds. However, the compound is not limited to these compounds.

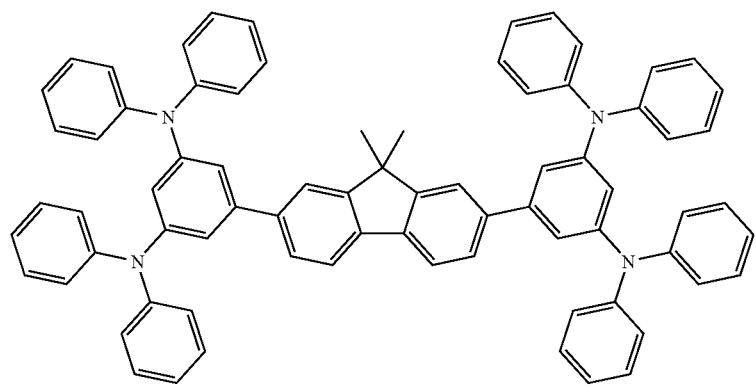
1
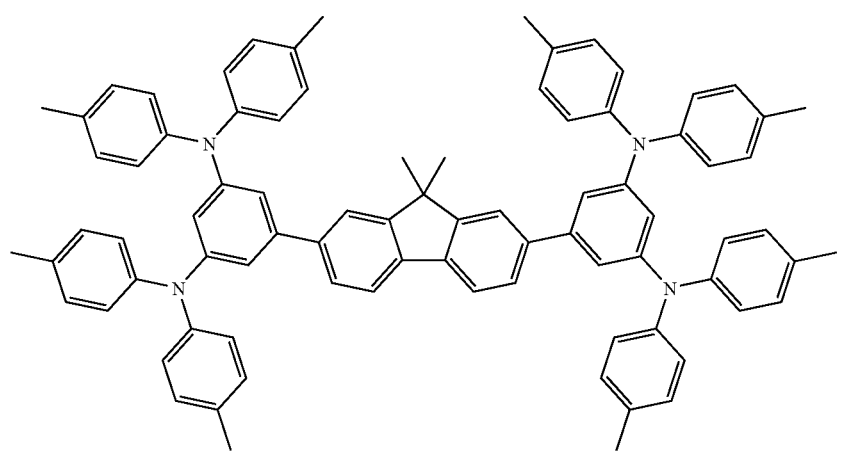
2
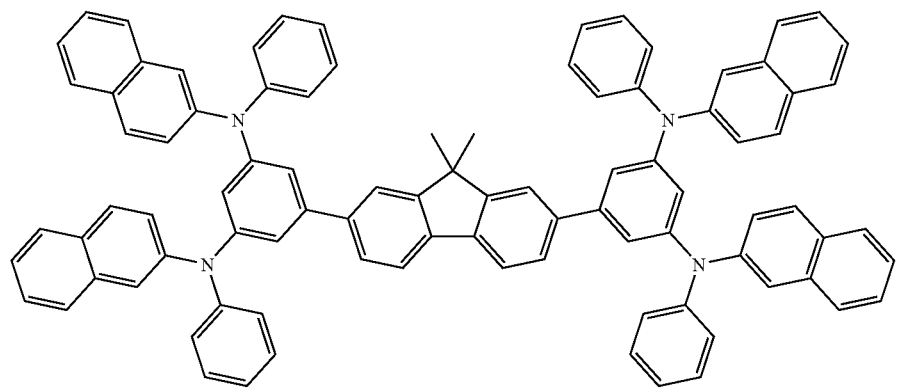
3

-continued
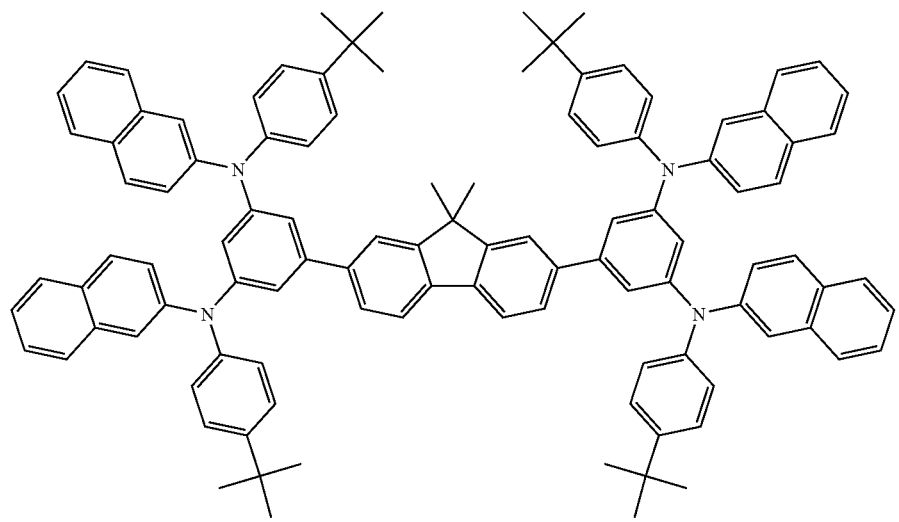
4
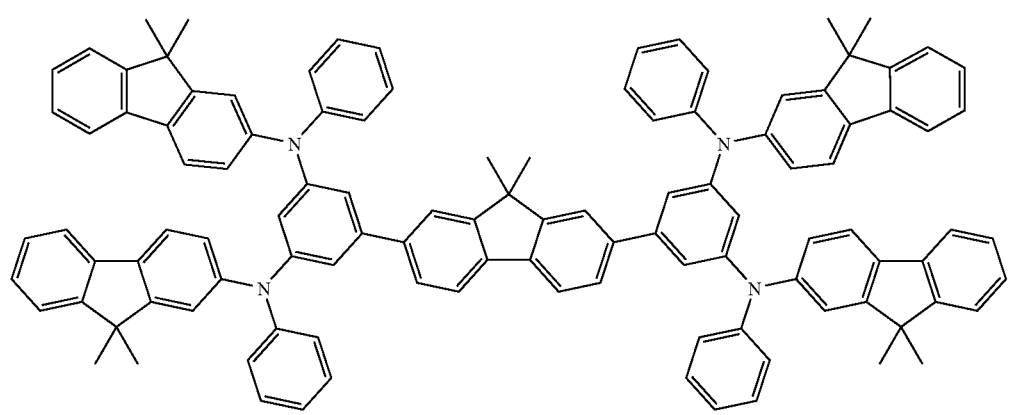
5
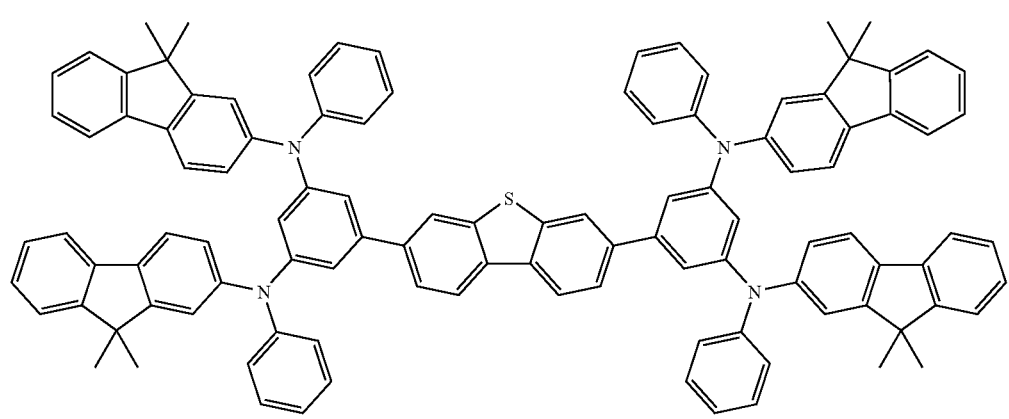
6

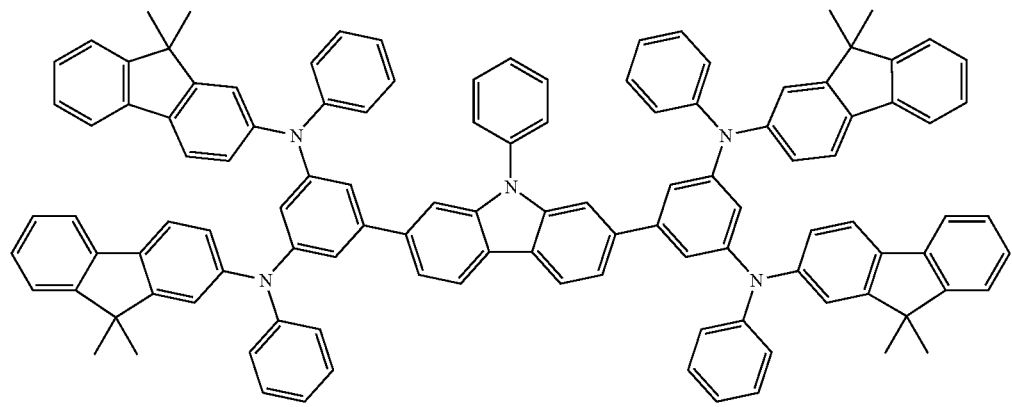
7
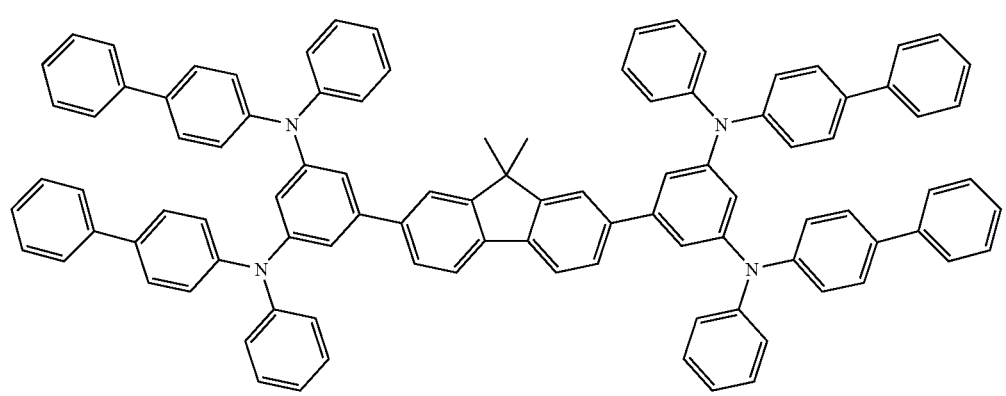
8
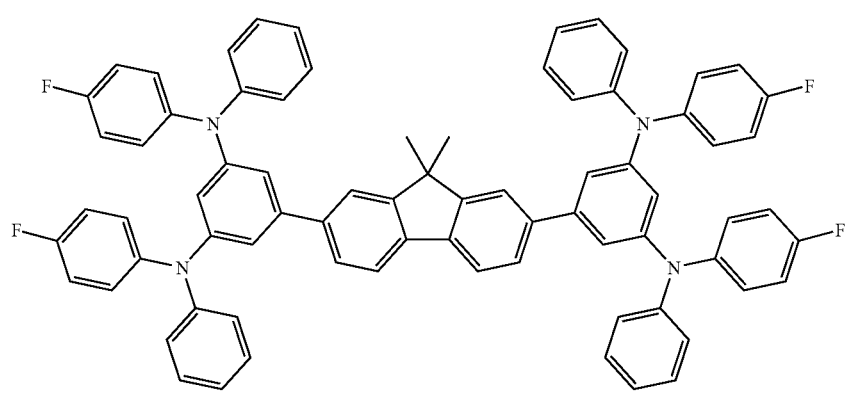
9
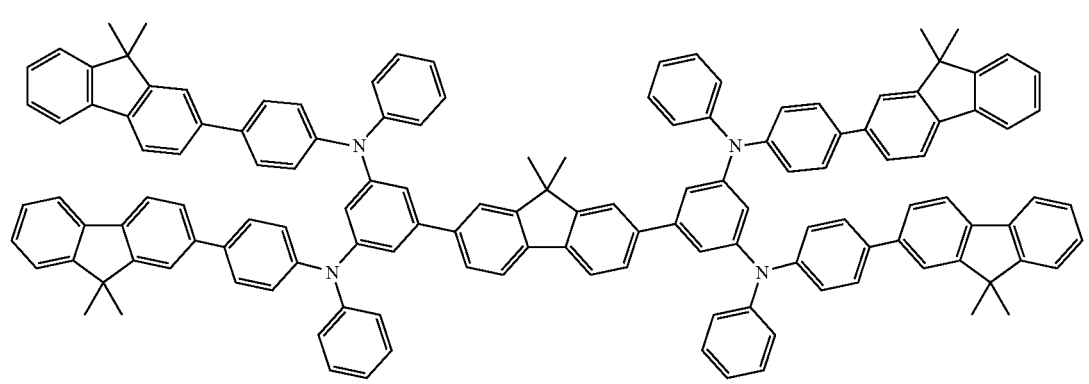
10

-continued
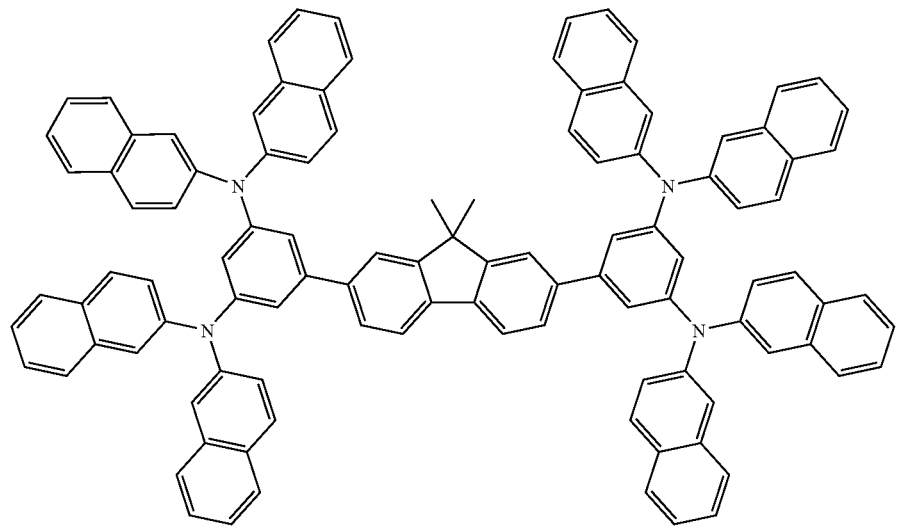
11
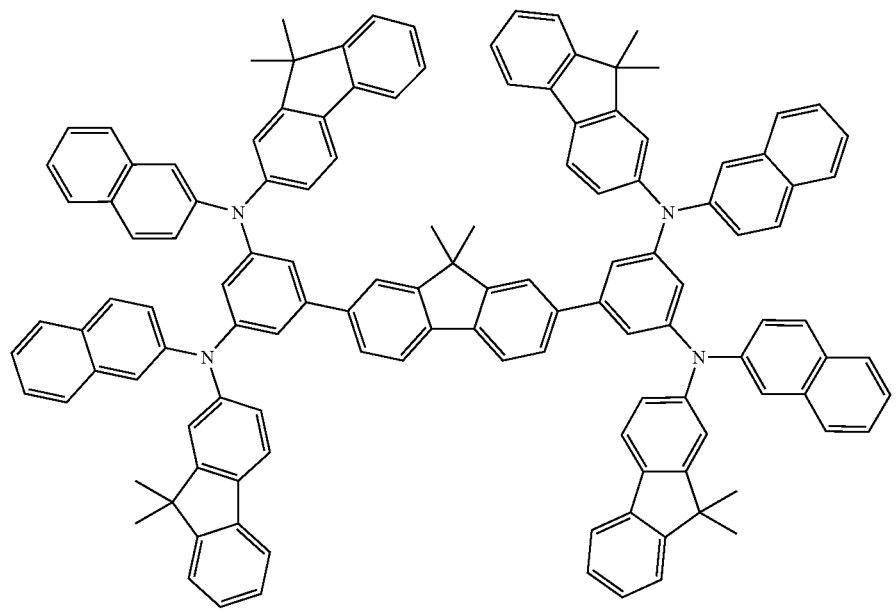
12
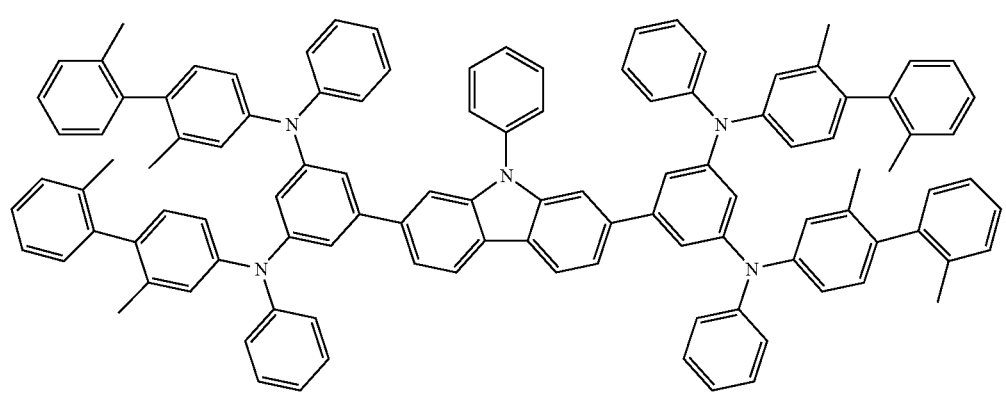
13

-continued
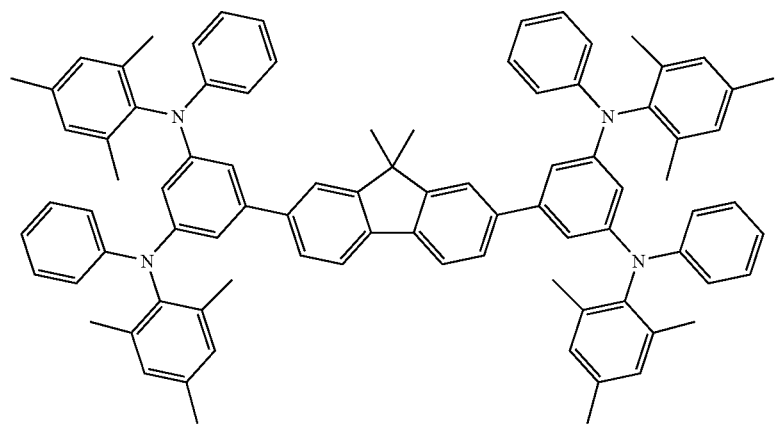
14
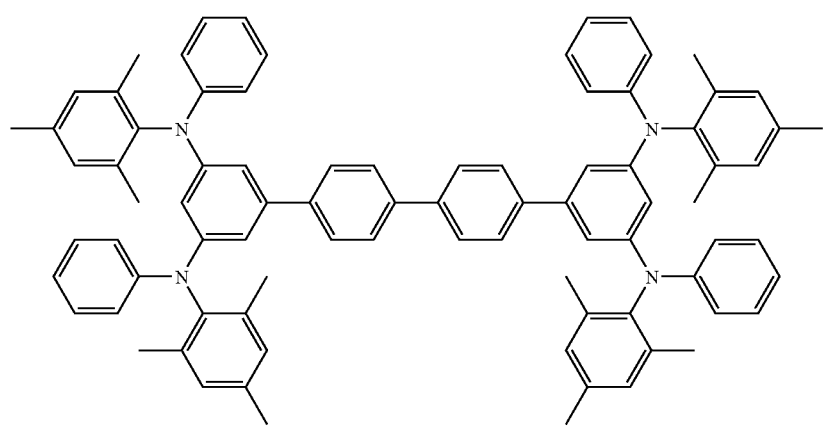
15
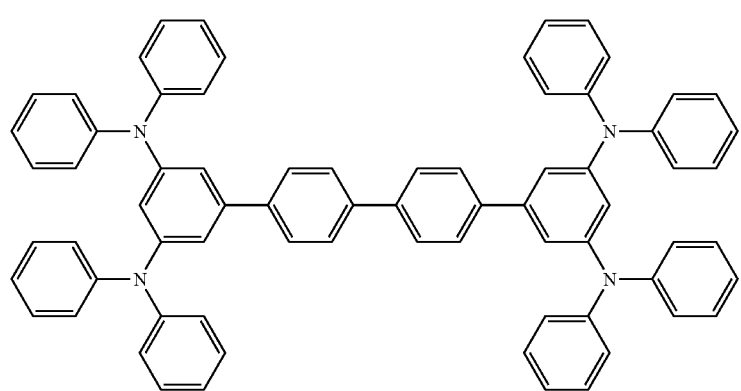
16
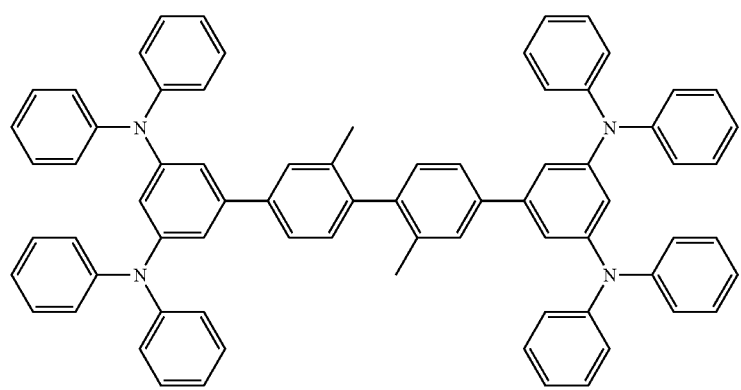
17

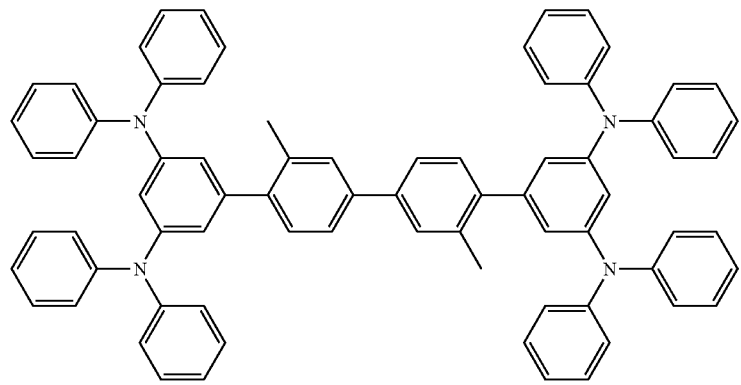
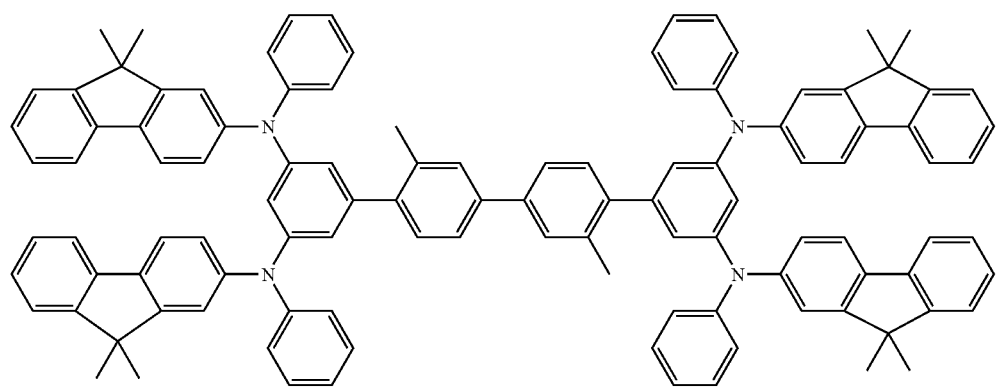
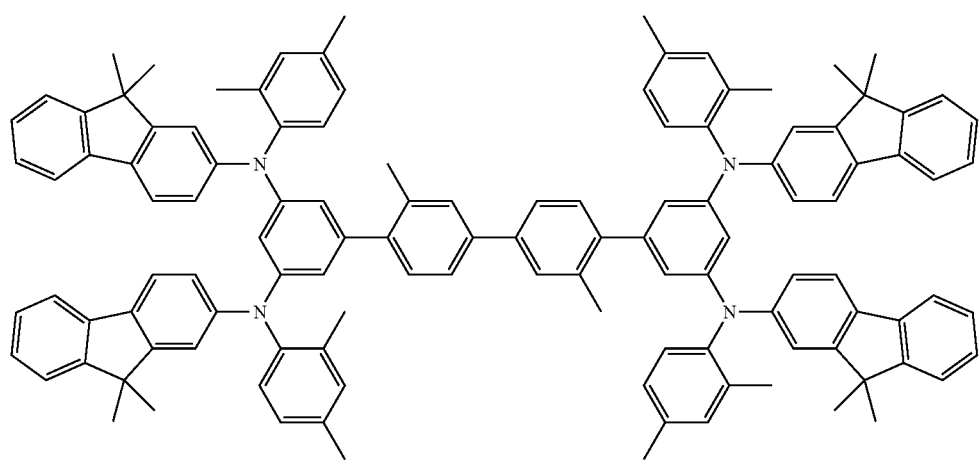

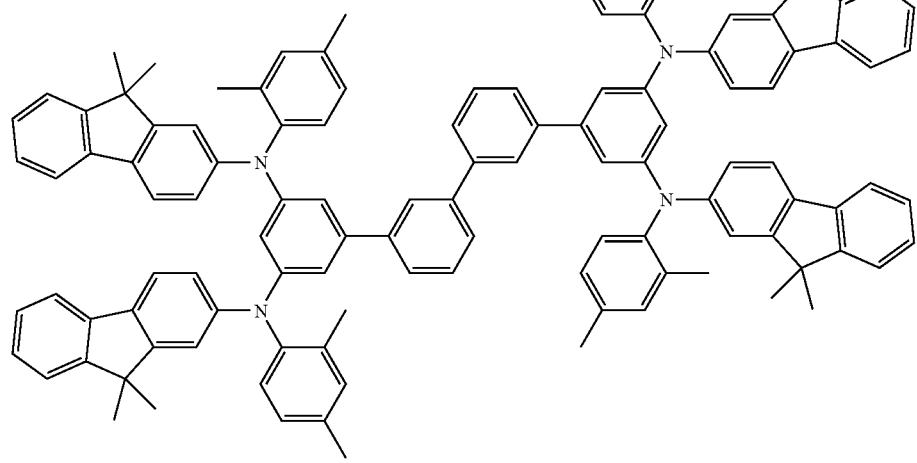
21
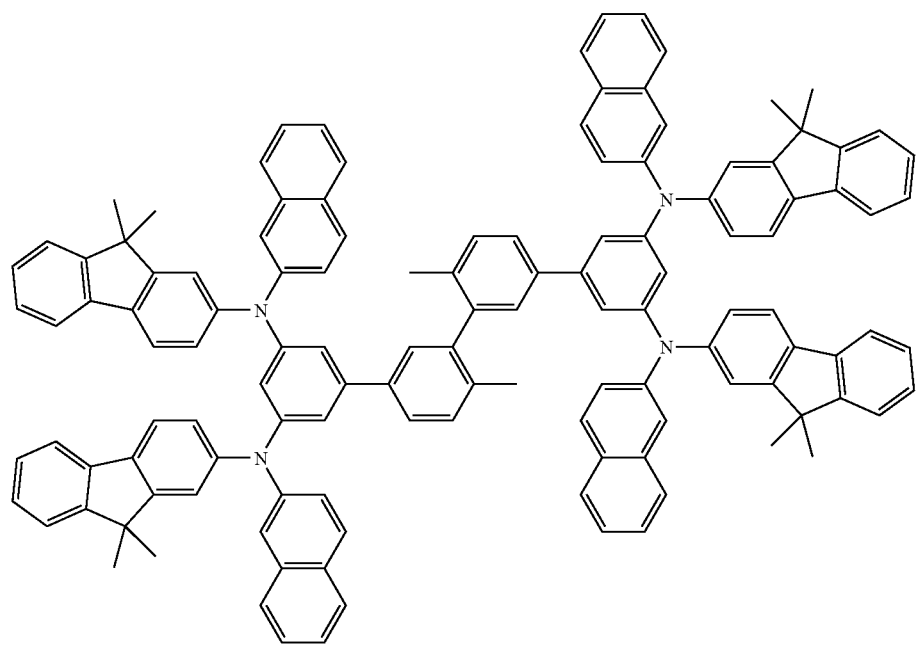
22

-continued
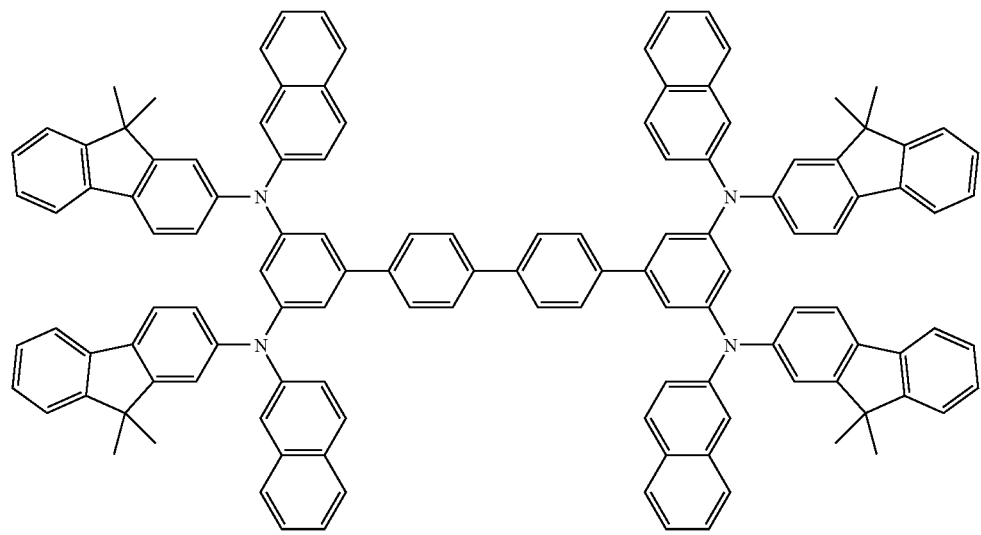
23
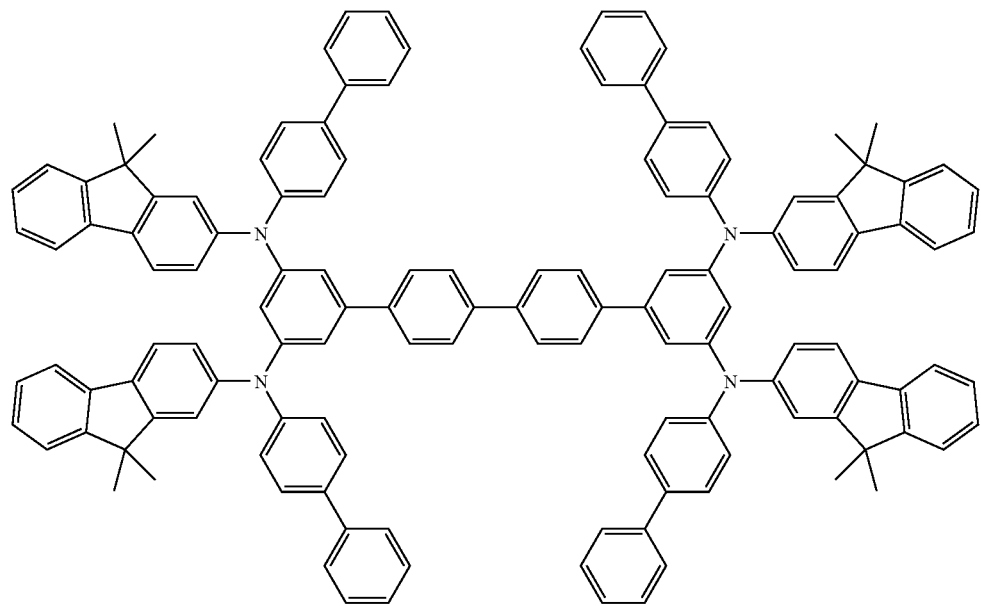
24

-continued
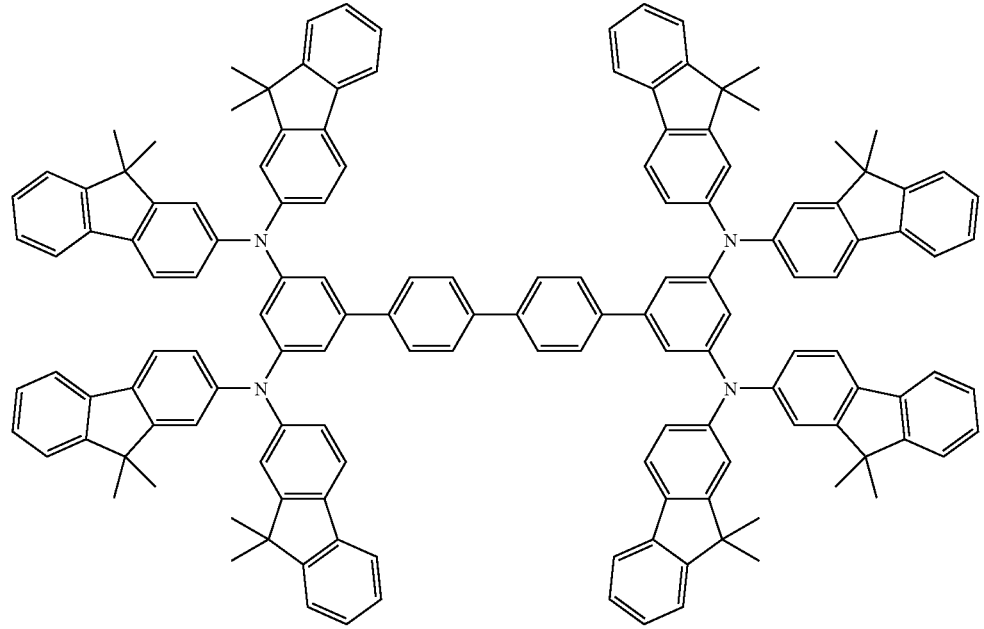
25
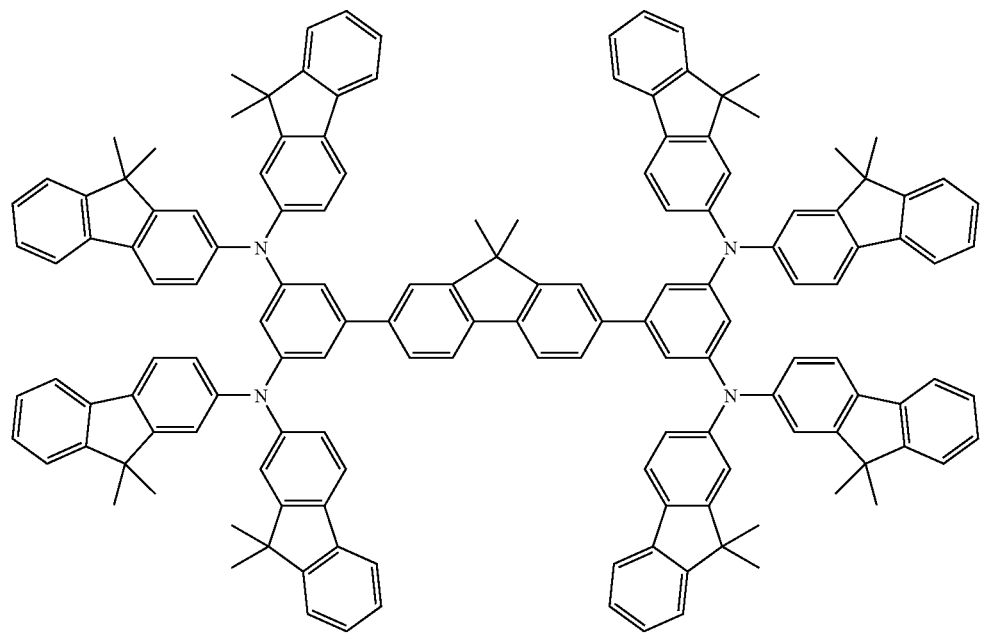
26

27
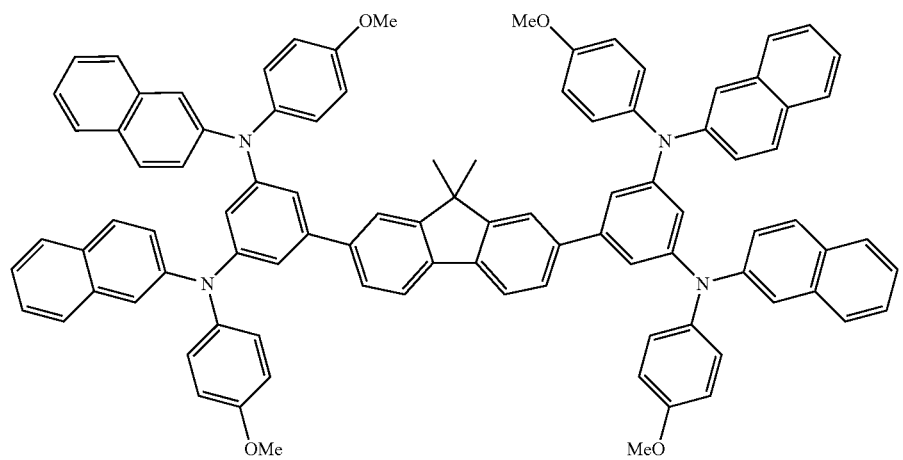
28
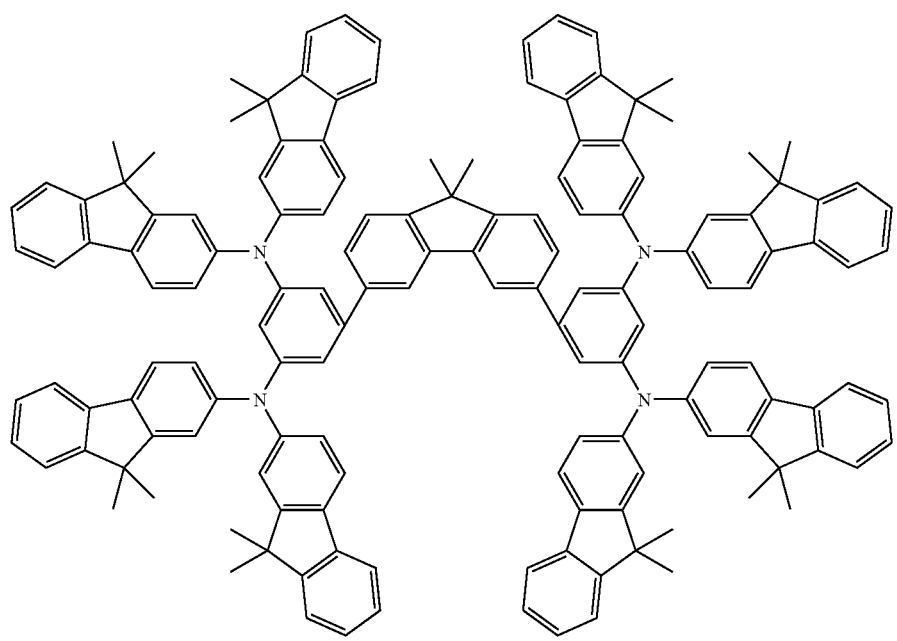
29
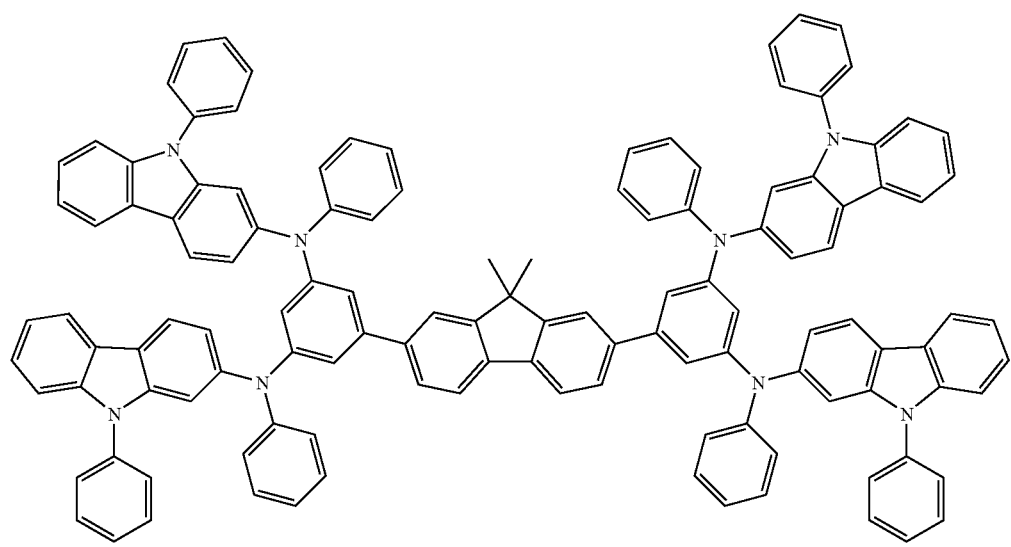

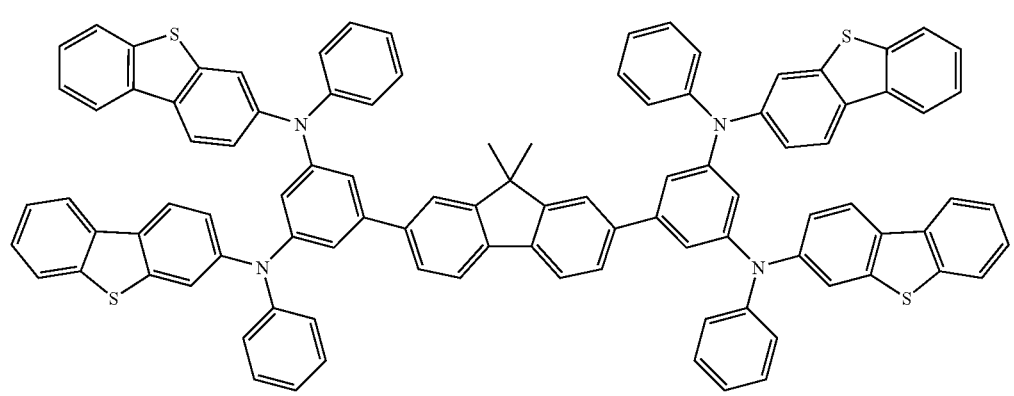
30
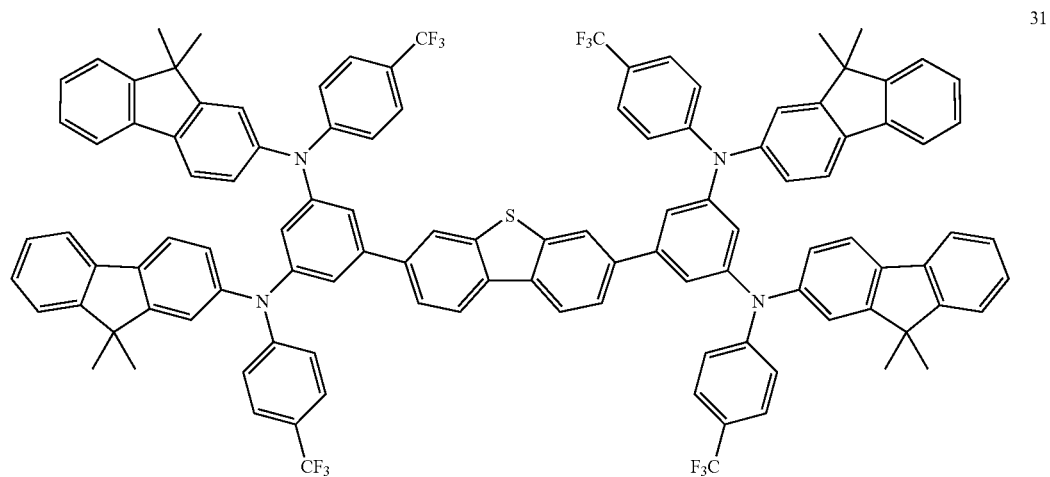
31
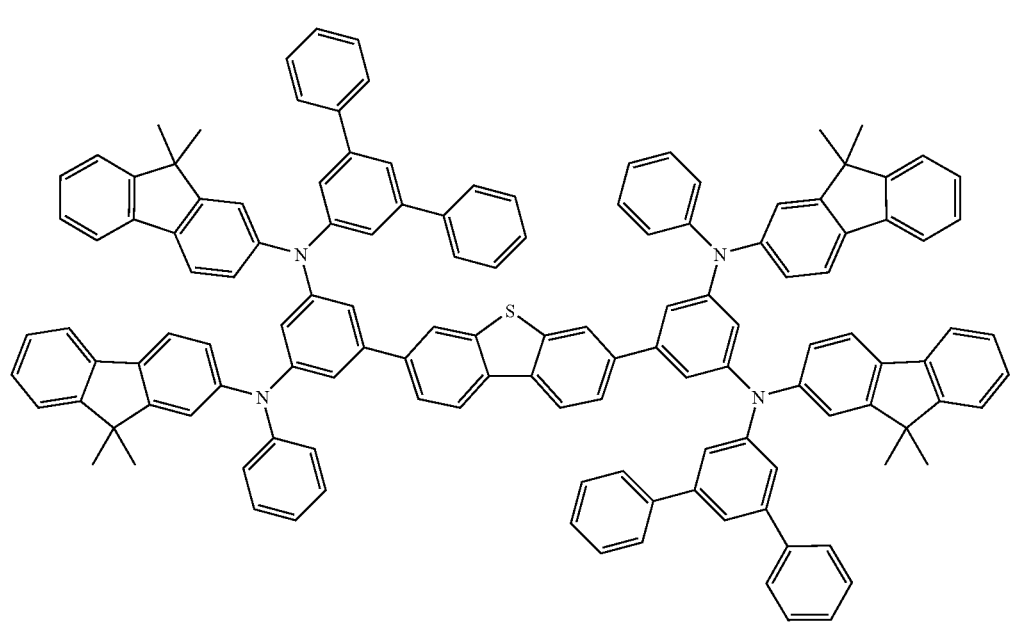
32

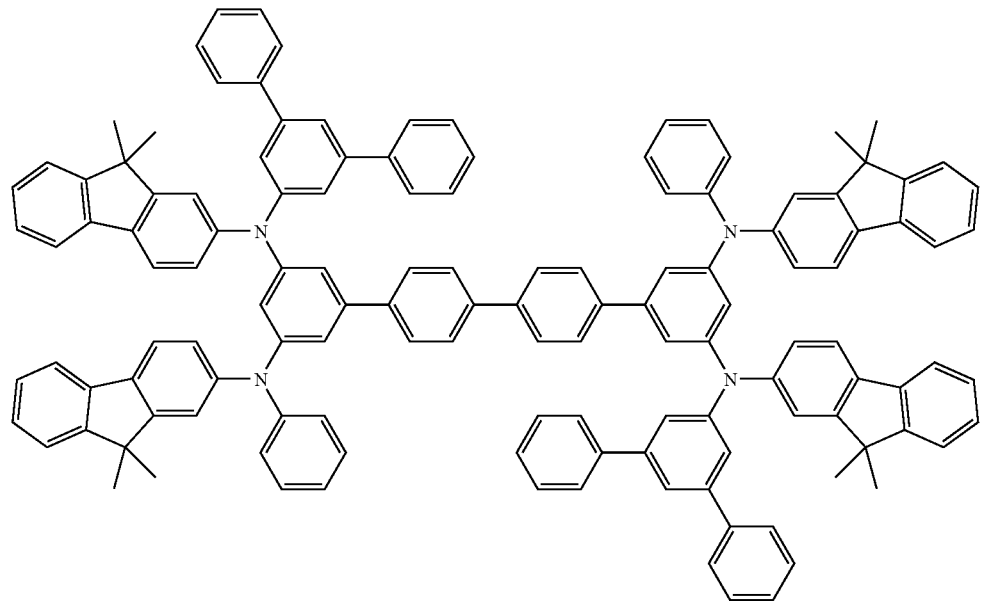
33
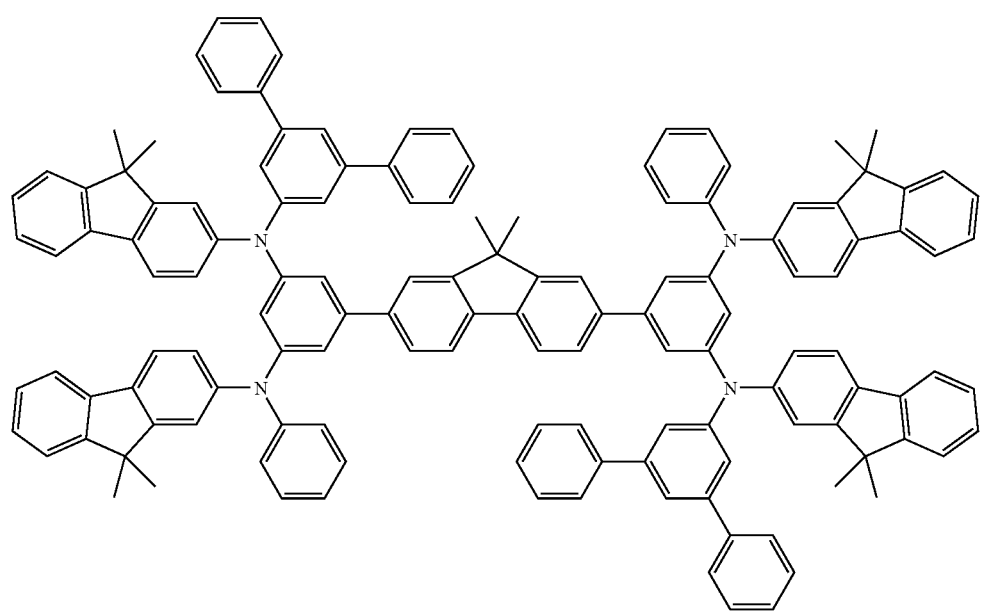
34

-continued
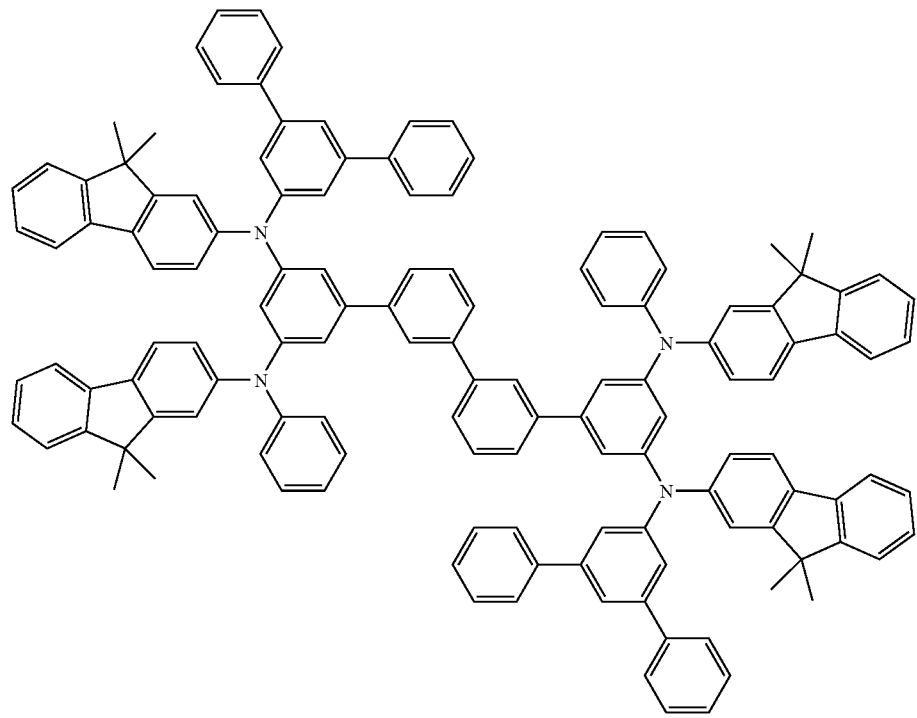
35
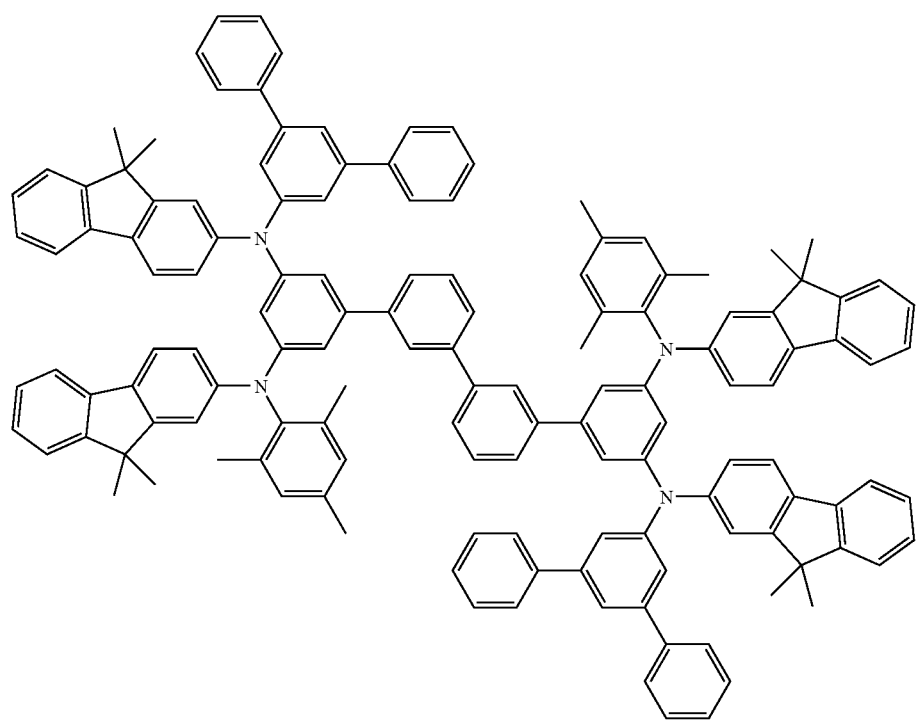
36

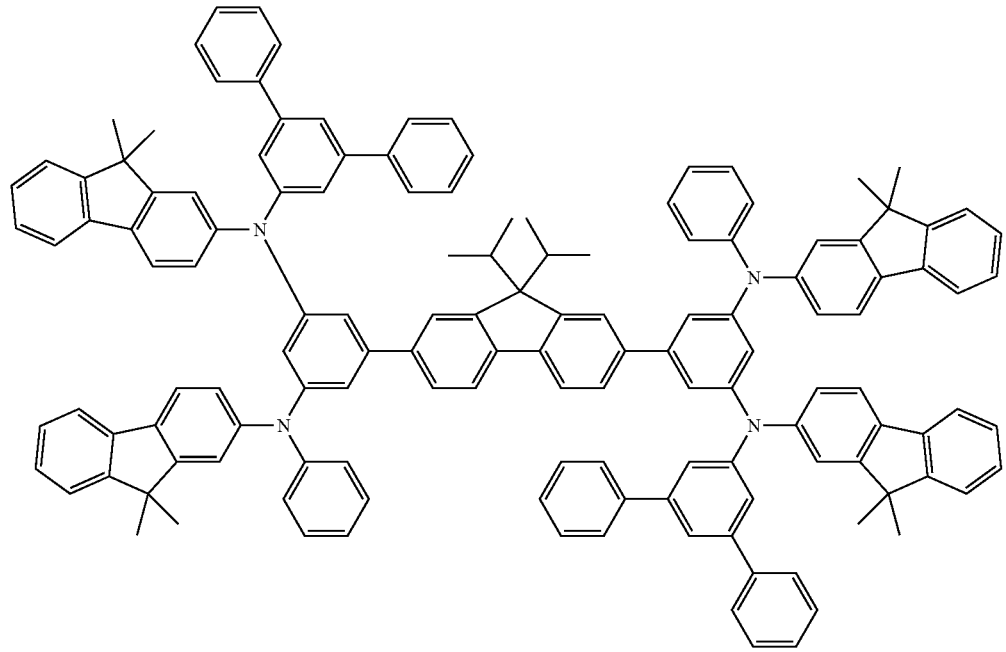
37
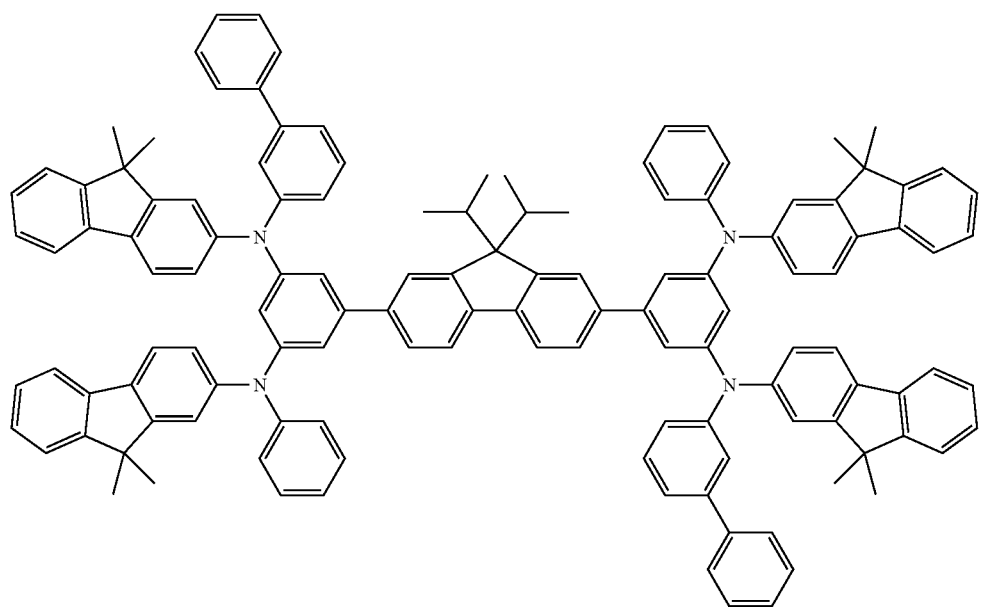
38

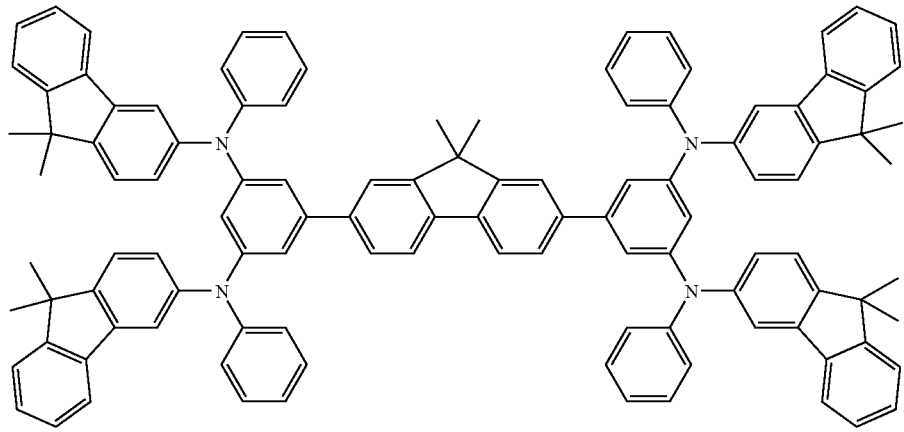
39
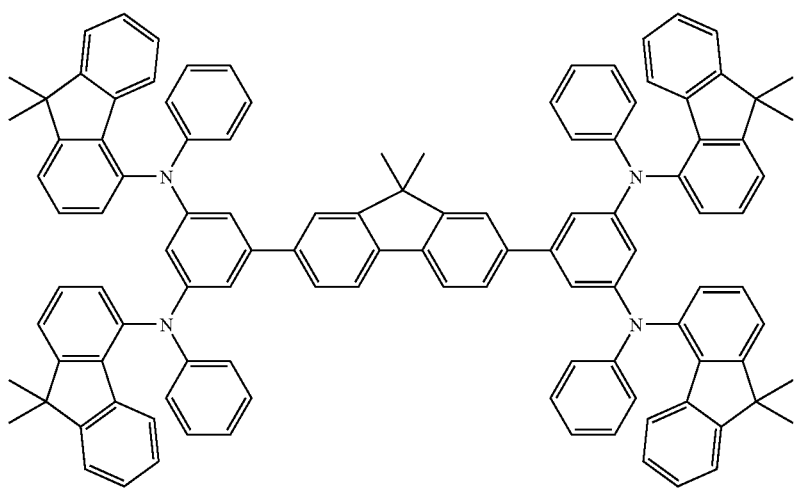
40
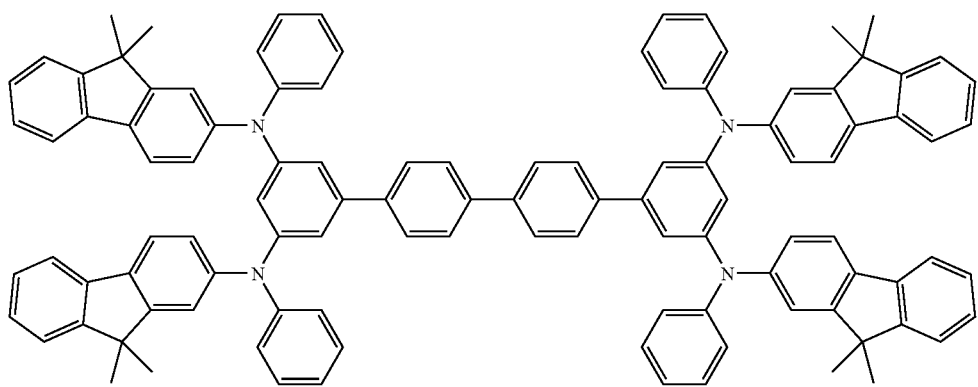
41

42
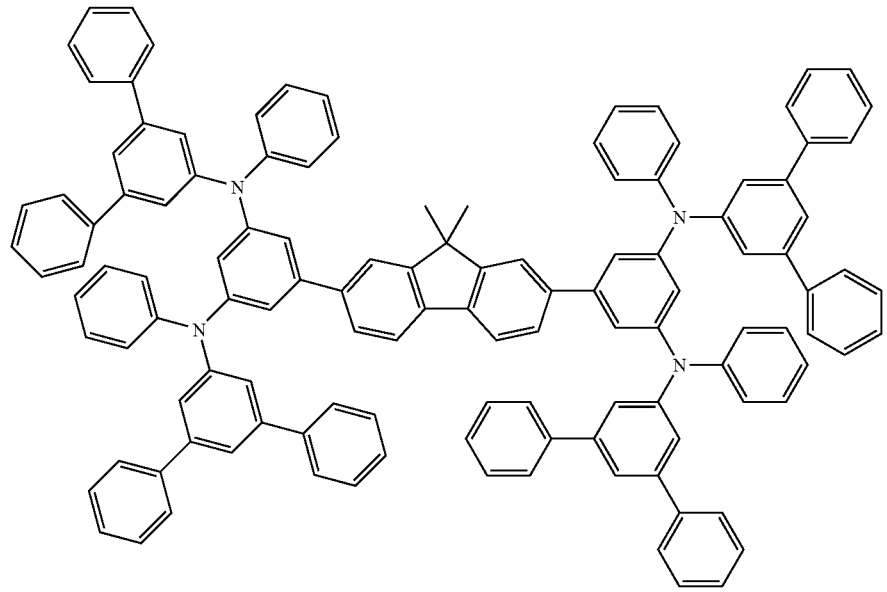
43
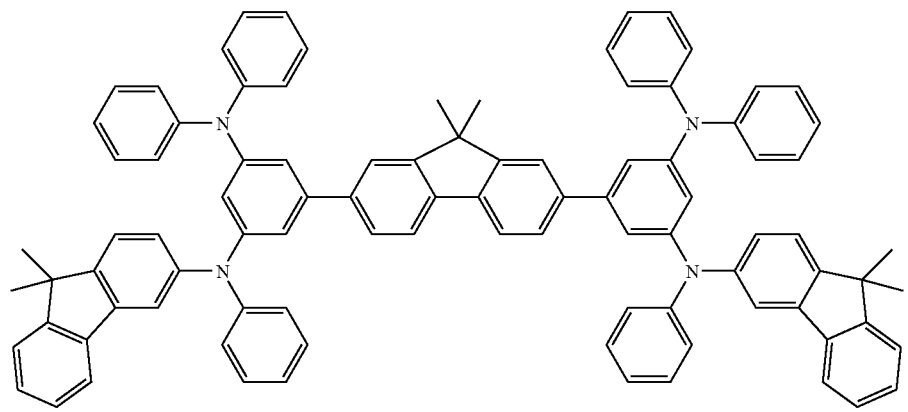
44
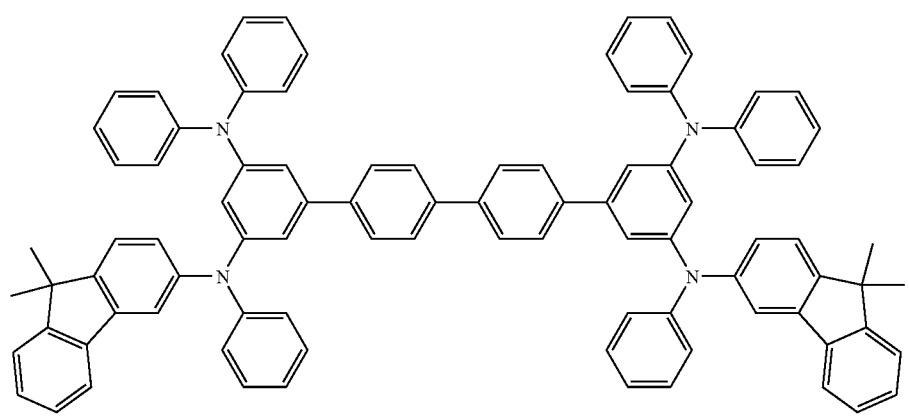

-continued
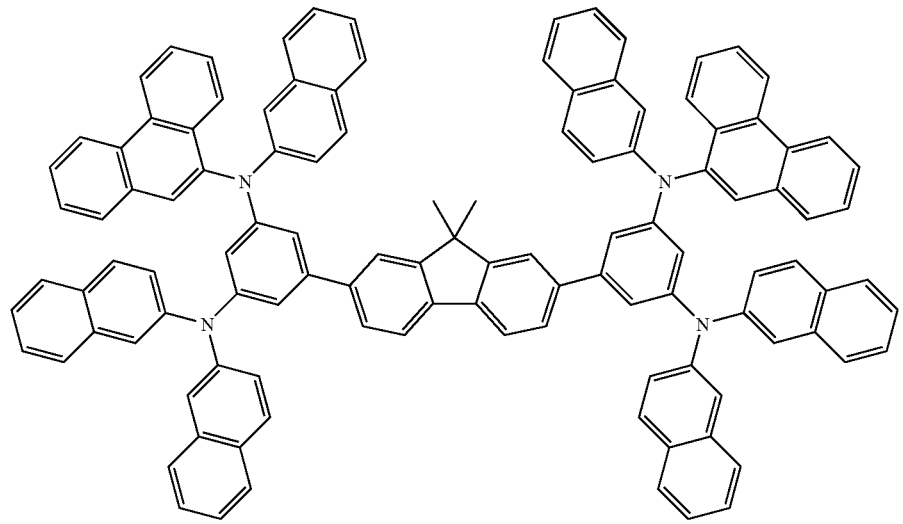
45
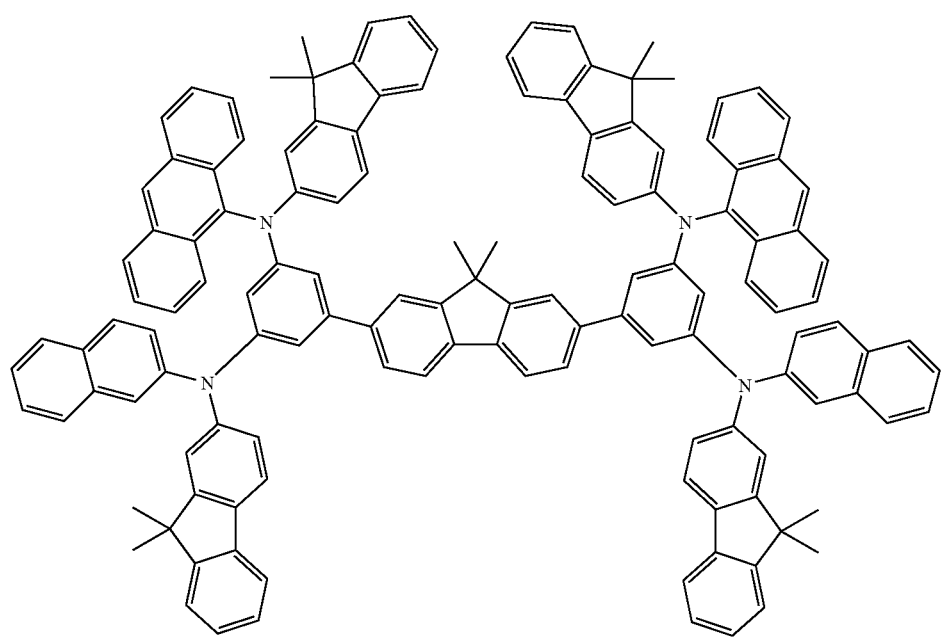
46
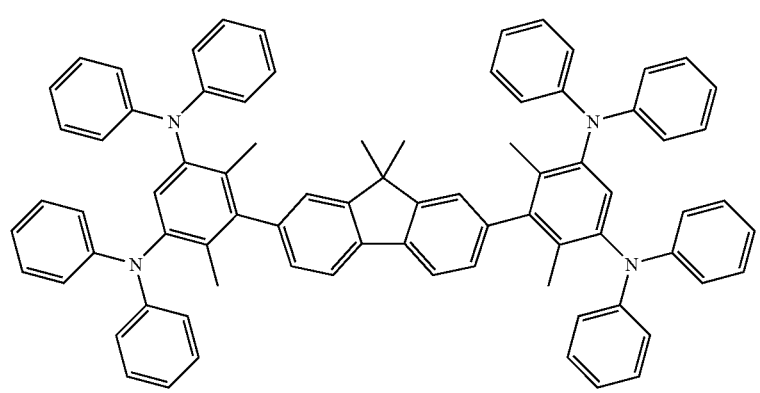
47

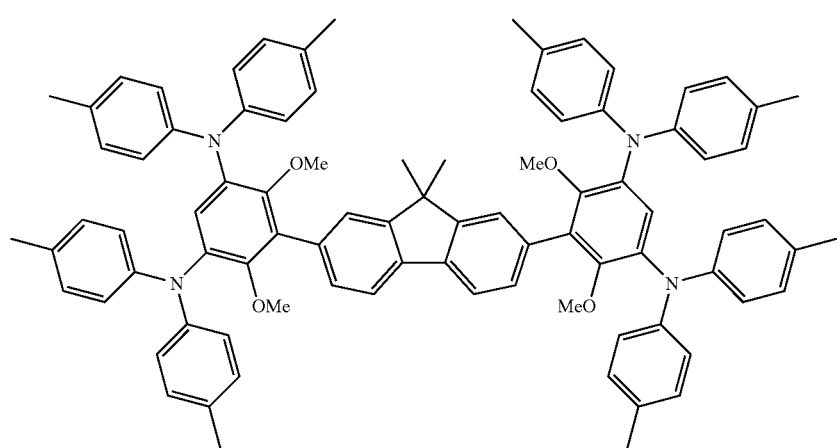
48
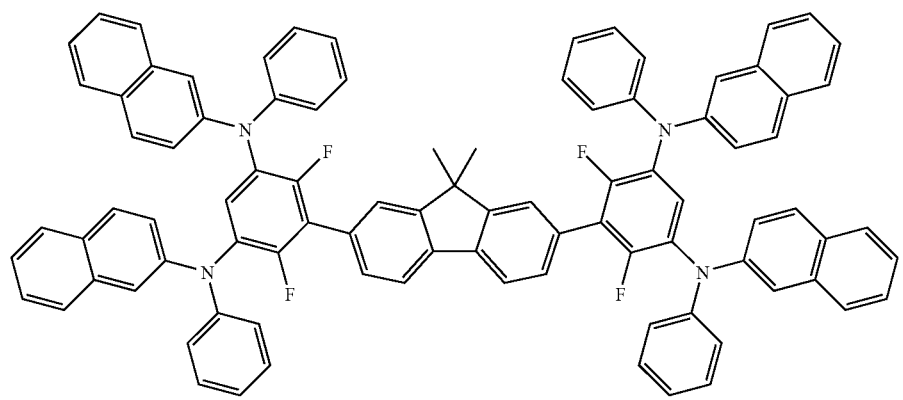
49
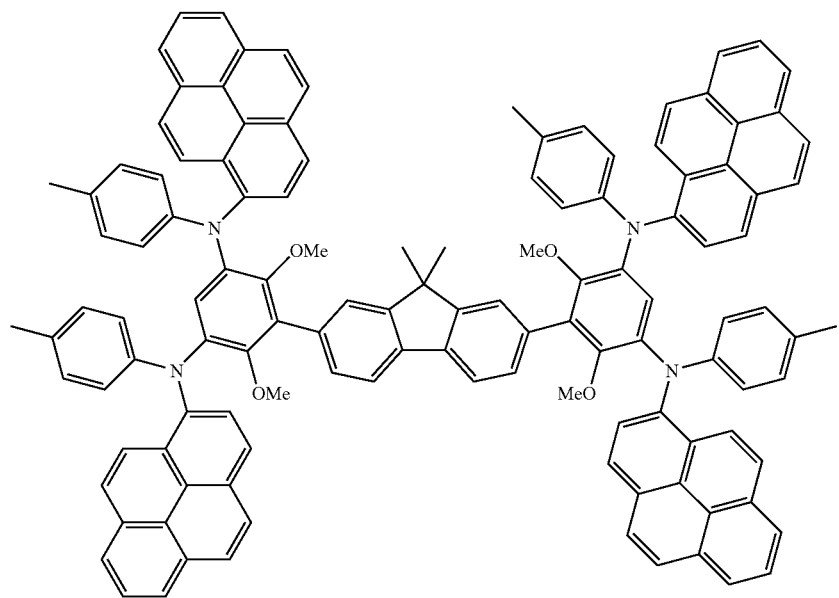
50

The amine compound of the present invention can be obtained by, for example, the following synthesis method, but a method by which the compound can be obtained is not limited to the following synthesis method.

An amino group can be introduced into a benzene derivative having a halogen atom by, for example, an amination reaction using a palladium catalyst. A coupling reaction between aryl derivatives can be performed by, for example, a Suzuki coupling reaction using an aryl halide and a palladium catalyst of an aryl boronic acid or an aryl boron ester (for example, Chem. Rev. 1995, 95, 2457-2483) or a Yamamoto reaction using a nickel catalyst (for example, Bull. Chem. Soc. Jpn. 51, 2091, 1978).

The amine compound of the present invention is a compound superior to any conventional compound in hole transport property, light emission property, and durability. In addition, the compound is useful in a layer containing an organic compound for an organic light-emitting device, in particular, as a hole transport layer or a hole injection layer and a light-emitting layer. In addition, a layer formed by, for example, a vacuum deposition method or a solution application method hardly causes, for example, crystallization, and is excellent in stability with elapse of time.

Next, an organic light-emitting device of the present invention will be described in detail.

The organic light-emitting device of the present invention includes at least a pair of electrodes including an anode and a cathode, and one or more layers each containing an organic compound, the one or more layers being interposed between the pair of electrodes. In addition, at least one layer of the one or more layers each containing an organic compound, desirably, the hole transport layer or hole injection layer and the light-emitting layer contain at least one kind of the amine compound of the present invention.

FIGS. 1 to 5 each illustrate a desirable example of the organic light-emitting device of the present invention.

FIG. 1 is a sectional view illustrating an example of the organic light-emitting device of the present invention. FIG. 1 illustrates a constitution in which an anode 2, a light-emitting layer 3, and a cathode 4 are sequentially provided onto a substrate 1. The light-emitting device to be used here is useful in a case where a compound having properties such as a hole-transporting ability, an electron-transporting ability, and light-emitting properties by itself alone is used or a case where compounds each having any one of the properties are used as a mixture.

Figure 2:
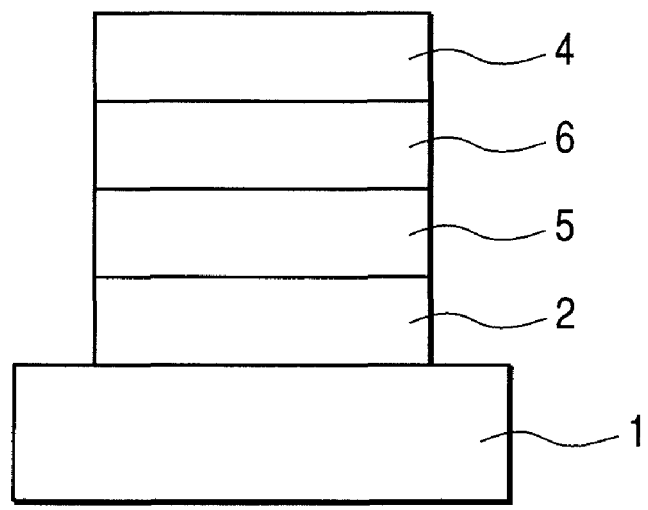
FIG. 2 is a sectional view illustrating another example of the organic light-emitting device according to the present invention.

FIG. 2 is a sectional view illustrating another example of the organic light-emitting device of the present invention. FIG. 2 illustrates a constitution in which the anode 2, a hole transport layer 5, an electron transport layer 6, and the cathode 4 are sequentially provided onto the substrate 1. In this case, a material having one or both of hole-transporting property and electron-transporting property is used as a light-emitting substance. This case is useful when the device is used in combination with a mere hole-transporting substance or electron-transporting substance having no light-emitting properties. In addition, in this case, a light-emitting layer is formed of one of the hole transport layer 5 and the electron transport layer 6.

Figure 3:
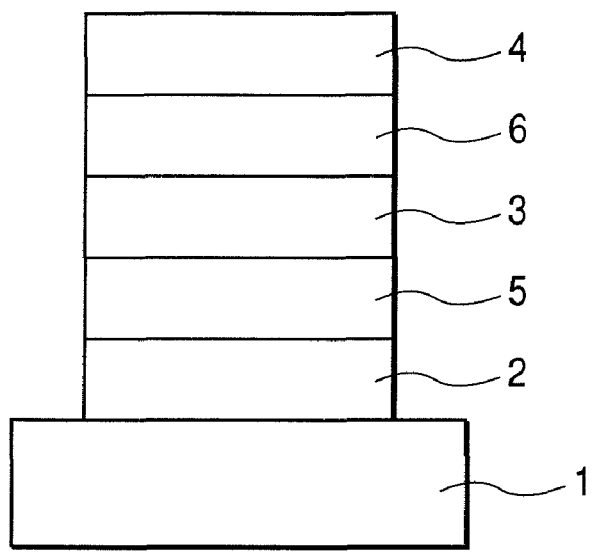
FIG. 3 is a sectional view illustrating another example of the organic light-emitting device according to the present invention.

FIG. 3 is a sectional view illustrating another example of the organic light-emitting device of the present invention. FIG. 3 illustrates a constitution in which the anode 2, the hole transport layer 5, the light-emitting layer 3, the electron transport layer 6, and the cathode 4 are sequentially provided onto the substrate 1. This constitution separates a carrier-transporting function and a light-emitting function. Thus, the device can be used in combination of a compound having a hole-transporting property, a compound having an electron-transporting property, and a compound having light-emitting property, so that the degree of freedom in selection of materials extremely increases. In addition, various compounds different from each other in emission wavelength can be used. As a result, the range of luminescent colors can be widened. Further, a luminous efficiency can be improved by effectively trapping each carrier or exciton in the central light-emitting layer 3.

Figure 4:
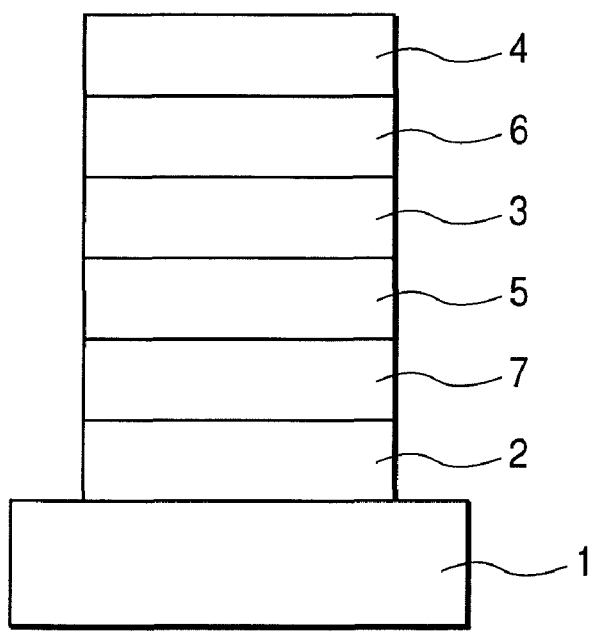
FIG. 4 is a sectional view illustrating another example of the organic light-emitting device according to the present invention.

FIG. 4 is a sectional view illustrating another example of the organic light-emitting device of the present invention. FIG. 4 illustrates a constitution different from that illustrated in FIG. 3 in that the hole injection layer 7 is inserted on the side of the anode 2. The constitution has an improving effect on adhesiveness between the anode 2 and the hole transport layer 5 or on hole injection property, and is effective for a reduction in driving voltage.

FIG. 5 is a sectional view illustrating another example of the organic light-emitting device of the present invention. FIG. 5 illustrates a constitution different from that illustrated in FIG. 3 in that a layer for inhibiting the escape of a hole or an exciton toward the side of the cathode 4 side (hole/exciton blocking layer 8) is inserted between the light-emitting layer 3 and the electron transport layer 6. The constitution is effective for an improvement in luminous efficiency when a compound having an extremely high ionization potential is used in the hole/exciton blocking layer 8.

It should be noted that the device constitutions illustrated in FIGS. 1 to 5 are merely very basic constitutions, and the constitution of an organic light-emitting device of the present invention is not limited to these constitutions. The device may adopt any one of various layer constitutions. For example, an insulating layer may be provided onto an interface between an electrode and an organic layer. Alternatively, an adhesive layer or an interference layer may be provided thereto. In addition, a hole transport layer includes two layers of different ionization potentials.

In the organic light-emitting device of the present invention, the amine compound of the present invention is desirably used as a component of a hole transport layer. A conventionally known low-molecular-weight-based or polymer-based hole transport compound, luminescent compound, electron transport compound, or the like can be used together with the compound of the present invention as required.

A layer containing the amine compound of the present invention and a layer including another organic compound are generally formed by a vacuum deposition method, an ionization deposition method, a sputtering method, or plasma. Alternatively, each layer is dissolved into an appropriate solvent to form a thin film by a known application method such as spin coating, a dipping method, a casting method, an LB method, an inkjet method, or the like. In particular, in the case where a thin film is formed by the application method, the film may also be formed in combination with an appropriate binder resin.

The binder resin may be selected from a wide variety of binder resins. Examples of the binder resin include, but not limited to, a polyvinyl carbazole resin, a polycarbonate resin, a polyester resin, a polyarylate resin, a polystyrene resin, an ABS resin, a polybutadine resin, a polyurethane resin, an acrylic resin, a methacrylic resin, a butyral resin, a polyvinyl acetal resin, a polyamide resin, a polyimide resin, a polyethylene resin, a polyethersulfone resin, a diallyl phthalate resin, a phenol resin, an epoxy resin, a silicone resin, a polysulfone resin, and a urea resin.

Each of those resins may be used alone, or one or more of them may be mixed as a copolymer. Further, an additive such as a known plasticizer, antioxidant, or ultraviolet absorber may be used together if required.

An anode material desirably has as large a work function as possible. Examples of the anode material include a metal such as gold, platinum, silver, copper, nickel, palladium, cobalt, selenium, vanadium, or tungsten. In addition, each of alloys thereof and metal oxides such as tin oxide, zinc oxide, indium oxide, indium tin oxide (ITO), and indium zinc oxide may be used. Further, a conductive polymer such as polyaniline, polypyrrole, polythiophene, or polyphenylene sulfide may also be used. Each of those electrode substances may be used alone, or two or more of them may be used in combination. Further, an anode may adopt a single layer construction or a multilayer construction.

On the other hand, a cathode material desirably has a small work function. Examples of the cathode material include: a metal such as lithium, sodium, potassium, calcium, magnesium, aluminum, indium, ruthenium, titanium, manganese, yttrium, silver, lead, tin, and chromium; and an alloy thereof such as lithium-indium, sodium-potassium, magnesium-silver, aluminum-lithium, aluminum-magnesium, and magnesium-indium. Alternatively, a metal oxide such as indium tin oxide (ITO) may also be used. Each of those electrode substances may be used alone, or two or more of them may be used in combination. Further, a cathode may adopt a single layer construction or a multilayer construction.

Further, at least either of an anode or a cathode may desirably be transparent or semi-transparent.

A substrate to be used in the present invention is, but not particularly limited to, an opaque substrate such as a metallic substrate or a ceramic substrate, or a transparent substrate of glass, quartz, or a plastic sheet is used. In addition, a luminescent color can be controlled by using a color filter film, a fluorescent color conversion filter film, a dielectric reflective film, or the like as the substrate. Alternatively, a device can be produced by producing a thin film transistor (TFT) on a substrate and by connecting the TFT to the substrate.

In addition, with regard to the direction of extracting light from the device, both a bottom emission constitution (constitution in which light is extracted from a substrate side) and a top emission constitution (constitution in which light is extracted from the side opposite to the substrate) are available.

It should be noted that the produced device may be provided with a protective layer or a sealing layer for the purpose of preventing the device from contacting with, for example, oxygen or moisture. Examples of the protective layer include: an inorganic material film such as a diamond thin film, a metal oxide, or a metal nitride; a polymer film such as a fluorine resin, polyparaxylene, polyethylene, a silicone resin, or a polystyrene resin; and a photocurable resin. In addition, the device itself may be covered with, for example, glass, a gas impermeable film, or a metal, and packaged with an appropriate sealing resin.

An ionization potential as specified in the present invention is defined as energy needed for an electron at the highest occupied molecular orbital (HOMO) level of a compound to be released to a vacuum level. Meanwhile, an electron affinity is defined as energy with which an electron at a vacuum level drops to the lowest unoccupied molecular orbital (LUMO) level of a substance to stabilize.

An ionization potential can be directly measured by ultraviolet photoelectron spectroscopy (UPS) or by a low-energy electron spectrometer (measuring instrument name AC-1, AC-2, or AC-3 manufactured by RIKENKIKI CO., LTD). Alternatively, the ionization potential can be determined from, for example, the measurement of an oxidation potential by a cyclic voltammetry method. In the present invention, a value for an ionization potential is a value measured with AC-1 manufactured by RIKENKIKI CO., LTD.

An electron affinity is defined by the following expression: (Electron affinity)=(Ionization potential)−(Band gap).

The band gap can be measured by, for example, a method involving: depositing an organic compound from the vapor onto glass to obtain a deposited film having a thickness of about 50 nm; measuring the absorption spectrum of the deposited film; and converting a wavelength Y (nm) of an absorption end of the spectrum into X (eV) (X can be determined by a conversion expression "X=1,240/Y").

It should be noted that an electron affinity can be determined also from the measurement of a reduction potential by a cyclic voltammetry method.

A method of determining an electron affinity adopted in the present invention involves calculating the electron affinity from a measured value for a band gap by light absorption and the above ionization potential. A spectrophotometer U-3010 (manufactured by Hitachi High-Tech Fielding Corporation) was used for measuring an absorption spectrum.

Hereinafter, the present invention will be described more specifically by way of examples. However, the present invention is not limited to these examples.

Example 1

Synthesis of Exemplified Compound 5 a) Synthesis of Intermediate Compound (1-3) (5-bromo-N1,N3-bis(9,9-dimethyl-fluorenyl)-N1, N3-diphenylbenzene-1,3-diamine)

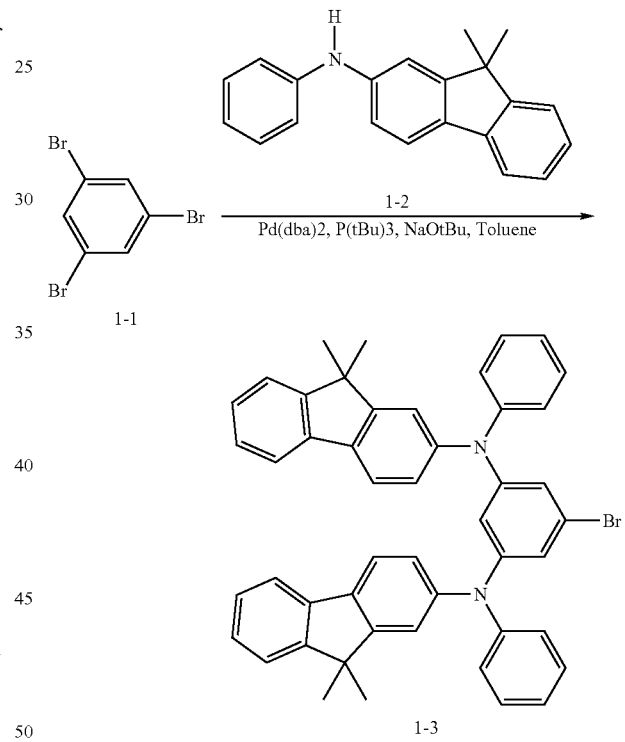

A 300-ml three-necked flask was prepared. 5.0 g (15.9 mmol) of Compound (1-1) (1,3,5-tribromobenzene) were loaded into the flask. In addition, 8.2 g (31.7 mmol) of Compound (1-2) (N-phenyl-N-(9,9-dimethyl-fluorenyl)amino group) and 3.04 g (31.7 mmol) of sodium tertiary butoxide were loaded into the flask. Further, 200 ml of toluene were loaded into the flask, and during the stirring in a nitrogen atmosphere at room temperature, 1.1 g (4.77 mmol) of tritertiarybutylphosphine were added to the mixture. Next, 0.91 g (31.7 mmol) of palladium dibenzylideneacetone was added to the mixture. The temperature of the mixture was increased to 80° C., and the mixture was stirred for 2 hours. After the reaction, an organic layer was extracted with toluene, dried with anhydrous sodium sulfate, and purified with a silica gel column (mixed developing solvent of heptane and toluene), whereby 3.68 g of Compound (1-3) (white crystal) were obtained (32.0% yield).

b) Synthesis of Exemplified Compound 5

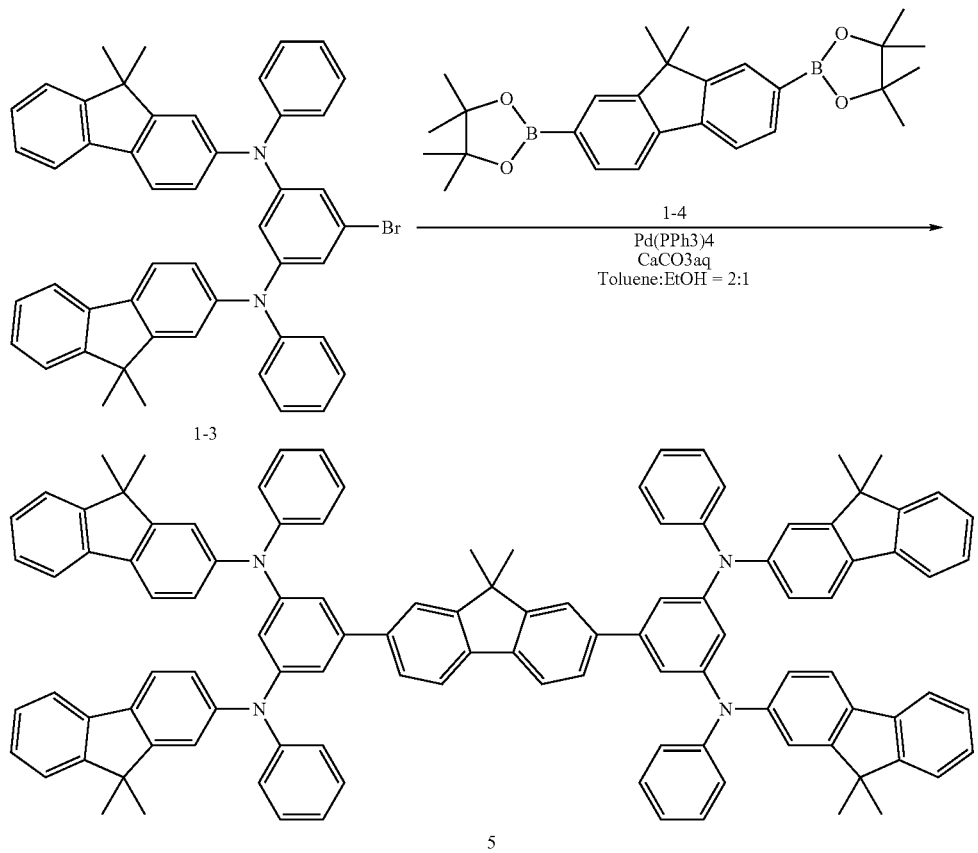

A 200-ml three-necked flask was prepared. 1.2 g (2.69 mol) of Compound (1-4) were loaded into the flask. Further, 3.89 g (5.38 mmol) of Compound (1-3) were loaded into the flask. Further, 100 ml of toluene and 50 ml of ethanol were loaded into the flask, and an aqueous solution prepared by dissolving 1 g of calcium carbonate in 20 ml of water was dropped while the mixture was stirred in a nitrogen atmosphere at room temperature. Next, 0.31 g (0.27 mmol) of tetrakis(triphenylphosphine)palladium(0) was added. The temperature of the resultant was increased to 80° C., and then the resultant was stirred for 6 hours. After the reaction, an organic layer was extracted with toluene, dried with anhydrous sodium sulfate, and purified with a silica gel column (mixed developing solvent of hexane and toluene), whereby 2.15 g of Exemplified Compound 5 (white crystal) were obtained (54% yield).

Matrix-assisted laser desorption/ionization time-of-flight mass spectrometry (MALDI-TOF MS) confirmed that the $M^+$ of the compound was 1478.7. Differential scanning calorimetry (DSC) was performed to confirm that the compound had a Tg of 174° C. It was confirmed that the compound had an ionization potential of 5.30 eV, an electron affinity of 2.22 eV, and a band gap of 3.08 eV.

Example 2

Synthesis of Exemplified Compound 41

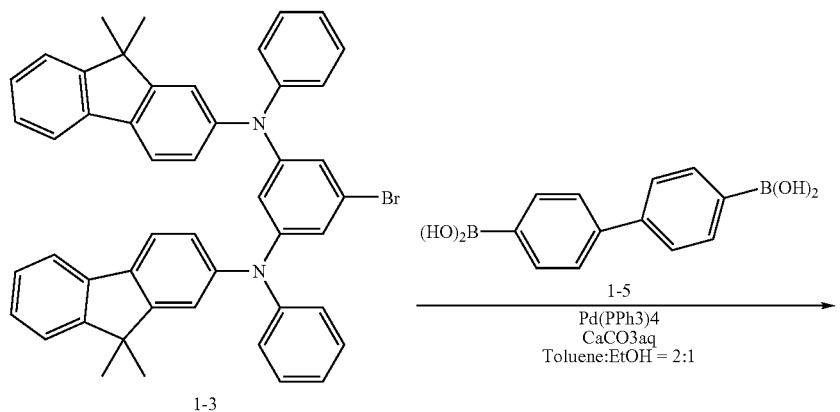

-continued

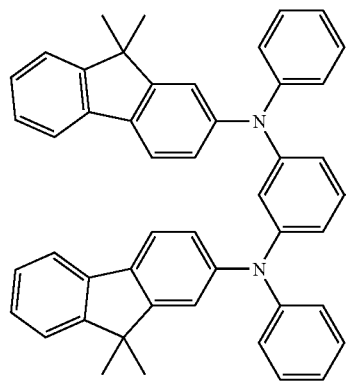
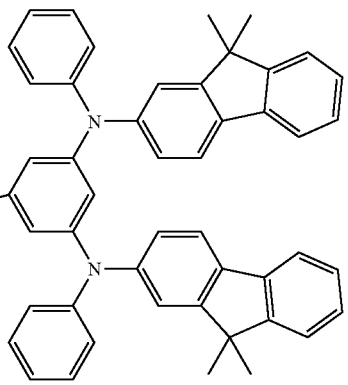

41

A 200-ml three-necked flask was prepared. 0.4 g (1.65 mol) of Compound (1-5) was loaded into the flask. Further, 2.4 g (3.3 mmol) of Compound (1-3) were loaded into the flask. Further, 100 ml of toluene and 50 ml of ethanol were loaded into the flask, and an aqueous solution prepared by dissolving 1 g of calcium carbonate in 20 ml of water was dropped while the mixture was stirred in a nitrogen atmosphere at room temperature. Next, 0.38 g (0.33 mmol) of tetrakis(triphenylphosphine)palladium(0) was added. The temperature of the resultant was increased to 80° C., and then the resultant was stirred for 6 hours. After the reaction, an organic layer was extracted with toluene, dried with anhydrous sodium sulfate, and purified with a silica gel column (mixed developing solvent of hexane and toluene), whereby 1.45 g of Exemplified Compound 41 (white crystal) were obtained (61% yield).

Matrix-assisted laser desorption/ionization time-of-flight mass spectrometry (MALDI-TOF MS) confirmed that the M+ of the compound was 1438.7. Differential scanning calorimetry (DSC) was performed to confirm that the compound had a Tg of 171° C. It was confirmed that the compound had an ionization potential of 5.30 eV, an electron affinity of 2.20 eV, and a band gap of 3.10 eV.

Example 3

An organic light-emitting device having a structure illustrated in FIG. 3 was produced by the following method.

Indium tin oxide (ITO) was formed by a sputtering method into a film having a thickness of 120 nm to serve as the anode 2 on a glass substrate as the substrate 1, and the resultant was used as a transparent, conductive supporting substrate. The substrate was subjected to ultrasonic cleaning with acetone and isopropyl alcohol (IPA) sequentially. Then, the substrate was subjected to boiling cleaning with IPA, followed by drying. Further, the substrate was subjected to UV/ozone cleaning. The resultant was used as a transparent conductive supporting substrate.

A chloroform solution was prepared by using Exemplified Compound 5 as a material for a hole transport layer in such a manner that the concentration of the compound would be 0.1 wt %.

The solution was dropped onto the above ITO electrode, and the whole was subjected to spin coating initially at a revolution speed of 500 RPM for 10 seconds and then at a revolution speed of 1,000 RPM for 1 minute, whereby a film was formed. After that, the resultant was dried for 10 minutes in a vacuum oven at 80° C., whereby the solvent in the thin film was completely removed. The hole transport layer 5 thus formed had a thickness of 11 nm.

Next, Compound 2-1 and Compound 3-1 shown below were co-deposited (at a weight ratio of 90:10) onto the hole transport layer 5 to provide the light-emitting layer 3 having a thickness of 20 nm. The layer was formed under conditions that a degree of vacuum upon deposition was $1.0 \times 10^{-4}$ Pa, and a film formation rate was 0.1 nm/sec.

2-1

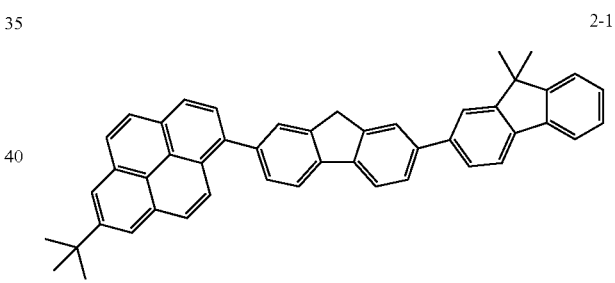

3-1

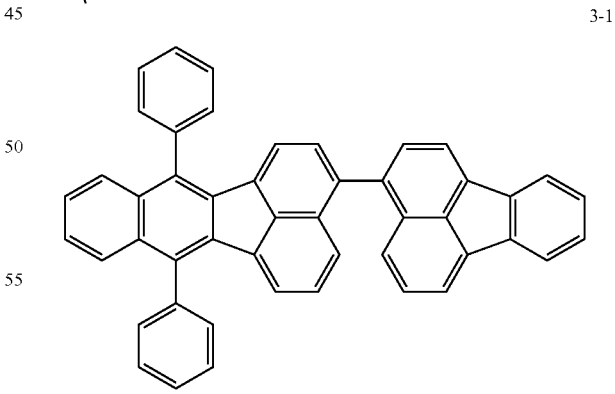

Further, bathophenanthroline (BPhen) was formed by a vacuum deposition method into a film having a thickness of 40 nm to serve as the electron transport layer 6. The film was formed under conditions that a degree of vacuum upon deposition was $1.0 \times 10^{-4}$ Pa, and a film formation rate was 0.2 to 0.3 nm/sec.

Next, a metal layer having a thickness of 0.5 nm was formed by a vacuum deposition method on the foregoing organic layer by using a deposition material formed of an aluminum-lithium alloy (having a lithium concentration of 1 atomic %). Further, an aluminum film having a thickness of 150 nm was provided by a vacuum deposition method. Thus, an organic light-emitting device using the aluminum-lithium alloy film as an electron injection electrode (cathode 4) was produced. The films were each formed under conditions that a degree of vacuum upon deposition was $1.0 \times 10^{-4}$ Pa, and a film formation rate was 1.0 to 1.2 nm/sec.

The obtained organic EL device was covered with a protective glass plate in a dry air atmosphere and sealed with an acrylic resin-based adhesive in order that the device might be prevented from deteriorating owing to the adsorption of moisture.

A voltage of 4.0 V was applied to the thus-obtained device while using the ITO electrode (anode 2) as a positive electrode and the Al electrode (cathode 4) as a negative electrode. As a result, the device was observed to emit blue light having an emission luminance of 480 cd/m².

Further, a voltage was applied for 100 hours while a current density was kept at 30 mA/cm² under a nitrogen atmosphere. As a result, the deterioration of the luminance after 100 hours as compared to an initial luminance was small.

Example 4

A light-emitting device was produced in the same manner as in Example 3 except that Exemplified Compound 41 was used instead of Exemplified Compound 5, and was evaluated in the same manner as in Example 3. As a result, the device was observed to emit blue light having an emission luminance of 520 cd/m² at an applied voltage of 4.0 V.

Further, a voltage was applied for 100 hours while the device was kept under a nitrogen atmosphere. As a result, the deterioration of the luminance after 100 hours as compared to an initial luminance was small.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims priorities from Japanese Patent Application No. 2006-320084 filed Nov. 28, 2006, which is hereby incorporated by reference herein.

What is claimed is:

1. An amine compound represented by the following general formula (1):

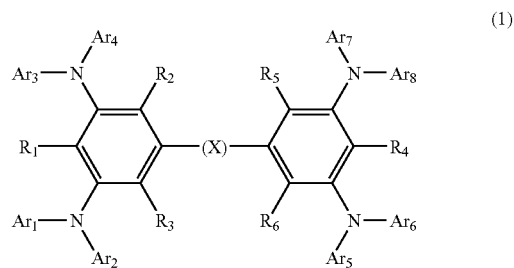

wherein:
$Ar_1$ to $Ar_8$ each independently represent a substituted or unsubstituted aryl group, or a substituted or unsubstituted heterocyclic group, and may be the same as or different from one another, and $Ar_1$ and $Ar_2$, $Ar_3$ and $Ar_4$, $Ar_5$ and $Ar_6$, or $Ar_7$ and $Ar_8$ may be bonded to each other to form a ring;
$R_1$ to $R_6$ each represent a hydrogen atom, a halogen atom, an alkyl group, an alkoxy group, an amino group, an aryl group, or a heterocyclic group, and may be the same as or different from one another, and the alkyl group, the alkoxy group, the amino group, the aryl group, and the heterocyclic group which are represented by $R_1$ to $R_6$ may have a substituent;
X represents a substituted or unsubstituted biphenylene or fluorenylene group, or a substituted or unsubstituted divalent heterocyclic group; and
at least one of $Ar_1$ to $Ar_8$ represents a fluorenyl group.

2. An organic light-emitting device, comprising:
a pair of electrodes including an anode and a cathode; and
an organic compound layer interposed between the pair of electrodes,
wherein the organic compound layer contains at least one kind of the amine compound according to claim 1.

3. An organic light-emitting device according to claim 2, wherein the organic compound layer is one of a hole transport layer and a hole injection layer.

* * * * *